(12) United States Patent
Rudolph et al.

(10) Patent No.: US 9,023,889 B2
(45) Date of Patent: May 5, 2015

(54) USE OF ASCORBIC ACID DERIVATIVES FOR THE FUNCTIONALIZATION OF MATRICES

(75) Inventors: Thomas Rudolph, Darmstadt (DE); Philipp Buehle, Darmstadt (DE); Herwig Buchholz, Frankfurt (DE)

(73) Assignee: Merck Patent GmbH, Darmstadt (DE)

( * ) Notice: Subject to any disclaimer, the term of this patent is extended or adjusted under 35 U.S.C. 154(b) by 1466 days.

(21) Appl. No.: 12/377,008

(22) PCT Filed: Jun. 27, 2007

(86) PCT No.: PCT/EP2007/005672
§ 371 (c)(1),
(2), (4) Date: Feb. 10, 2009

(87) PCT Pub. No.: WO2008/017346
PCT Pub. Date: Feb. 14, 2008

(65) Prior Publication Data
US 2010/0167936 A1    Jul. 1, 2010

(30) Foreign Application Priority Data

Aug. 11, 2006  (DE) .......................... 10 2006 037 724

(51) Int. Cl.
| A61K 8/67 | (2006.01) |
| A61Q 19/00 | (2006.01) |
| C07D 307/62 | (2006.01) |
| C07D 405/12 | (2006.01) |
| C07D 407/12 | (2006.01) |

(52) U.S. Cl.
CPC ................ A61K 8/676 (2013.01); A61Q 19/00 (2013.01); C07D 307/62 (2013.01); C07D 405/12 (2013.01); C07D 407/12 (2013.01)

(58) Field of Classification Search
None
See application file for complete search history.

(56) References Cited

U.S. PATENT DOCUMENTS

| 2,150,140 A | 3/1939 | Warnat |
| 4,179,445 A | 12/1979 | Sieb et al. |
| 4,329,290 A * | 5/1982 | Sawyer et al. ................. 549/316 |
| 4,560,703 A | 12/1985 | Fukushima et al. |
| 5,536,500 A | 7/1996 | Galey et al. |
| 5,563,056 A | 10/1996 | Swan et al. |
| 6,132,916 A | 10/2000 | Ueda et al. |
| 6,346,254 B1 | 2/2002 | Streicher et al. |
| 7,674,848 B2 * | 3/2010 | Lin ............................. 524/318 |
| 2003/0153736 A1 | 8/2003 | Champion et al. |
| 2005/0164136 A1 | 7/2005 | Ramsden et al. |
| 2006/0100177 A1 | 5/2006 | Nishimura |

FOREIGN PATENT DOCUMENTS

| EP | 104631 A2 | 9/1983 |
| EP | 0 664 290 | 1/1995 |
| EP | 0917 871 A2 | 10/1998 |
| EP | 0 875 246 A | 11/1998 |
| EP | 1 527 777 A | 5/2005 |
| ES | 2 189 602 A1 | 7/2003 |
| ES | 2189602 * | 7/2003 |
| JP | 60-4127 | 1/1985 |
| WO | WO 2006/018104 | 2/2006 |

OTHER PUBLICATIONS

International Search Report of PCT/EP2007/005672 Date of Completion Nov. 9, 2009, Date of Mailing Nov. 18, 2009 , 2 pages, Authorized Officer Nathalie Sala-Jung.
Lehrbuch der Lebens-mittelchemie, Springer-Verlag, D. Belitz, W. Grosch, 1987, 3. Auflage, S. 336-338.
Biotechnology Letters 22, 2000, "Enzymatic esterification of bixin L-ascorbic acid," pp. 165-168, C.Humeau et al.
Biochem J., 1994, 300, "Structural requirements for the utilization of ascorbate analogues in the prolyl 4-hydroxylase reaction," pp. 75-79, g. G. Tschank et al.
English Abstract of JP Publication No. JP 60-4127; Publication Date: Jan. 10, 1985. Applicant: Daikin Ind Ltd.

* cited by examiner

*Primary Examiner* — Traviss C McIntosh, III
(74) *Attorney, Agent, or Firm* — Millen, White, Zelano & Branigan, P.C.

(57) ABSTRACT

The invention relates to the use of at least one ascorbic acid derivative for the fictionalization of matrices, and to specific ascorbic acid derivatives and processes for the preparation thereof.

25 Claims, 1 Drawing Sheet

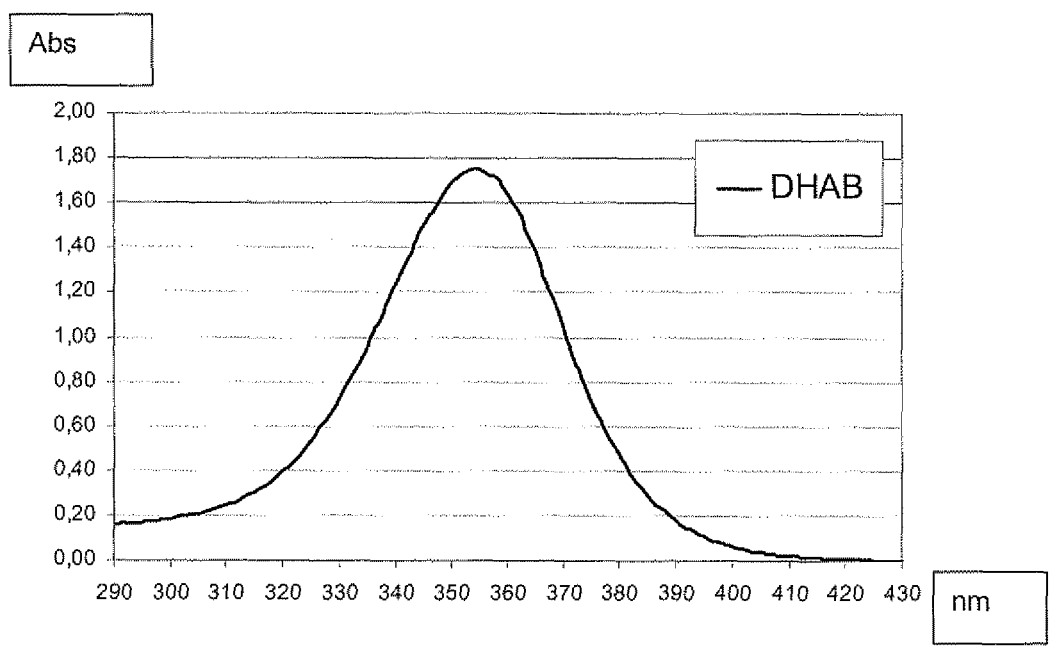

USE OF ASCORBIC ACID DERIVATIVES FOR THE FUNCTIONALIZATION OF MATRICES

The invention relates to the use of at least one ascorbic acid derivative for the functionalisation of matrices, and to specific ascorbic acid derivatives and processes for the preparation thereof.

The functionalisation according to the invention of protein-like matrices, in particular the skin, hair and/or nails, is carried out by covalent anchoring or strong electrostatic interaction. This results in immobilisation of the desired active compounds, for example UV filters, dyes, or enables controlled release of active compounds, for example for pharmacological, antimicrobial, fungicidal, herbicidal, insecticidal or cosmetic active compounds or for X-ray contrast agents.

A preferred area of application of the use according to the invention is UV protection. The human skin is subject to certain ageing processes, some of which are attributable to intrinsic processes (chronoageing) and some of which are attributable to exogenous factors (environmental, for example photoageing).

The exogenous factors include, in particular, sunlight or artificial radiation sources having a comparable spectrum, and compounds which are able to form due to the radiation, such as undefined reactive photoproducts, which may also be free radicals or ionic.

A multiplicity of organic and inorganic UV filters and antioxidants which are able to absorb UV radiation and scavenge free radicals is known. They are thus able to protect the human skin. These compounds catalyse the trans-formation of UV light into heat.

Owing to poor skin adhesion, however, the duration of protection is limited, in particular since conventional UV filters can be washed off very easily, for example by sweat or water.

It is a strategy, known, for example, from WO 2006/018104, to derivatise UV filters or self-tanning substances in such a way that they can bond covalently to the stratum corneum of the epidermis via a reactive moiety and thus functionalise the skin with the UV filter or self-tanning agent. For effective bonding to proteins and amino acids in the outer layers of the skin, it is necessary for the corresponding UV filter derivatives, or derivatives of other active compounds, such as pharmacological, antimicrobial, fungicidal, herbicidal, insecticidal or cosmetic active compounds, X-ray contrast agents or dyes, to have the highest possible reactivity of their bonding-capable moieties.

There is therefore increasing demand for skin-tolerated compounds which are able to functionalise protein-containing matrices and can be incorporated in a suitable manner into cosmetic or pharmacological compositions.

Surprisingly, it has now been found that ascorbic acid derivatives, in particular ascorbic acid derivatives which are substituted in the 6- and/or 5-position by active-compound radicals, are highly suitable for the functionalisation of matrices. Preferred matrices here are skin, hair and/or nails, where the general principle can also be applied to the functionalisation of synthetic polymer matrices containing amino groups or thiol groups, isolated proteins or gelatine. The products formed by bonding to such matrices can also themselves be used as cosmetic active compounds for the preparation of cosmetic agents. Both D- and also L-ascorbic acid, or mixtures thereof, can be derivatised in accordance with the invention.

The invention therefore relates firstly to the use of at least one ascorbic acid derivative, in particular ascorbic acid derivatives which are substituted in the 6- and/or 5-position by active-compound radicals, for the functionalisation of matrices.

It is known that ascorbic acid (vitamin C), often employed as natural anti-oxidant in the cosmetics or food industry, undergoes considerable losses due to vitamin C degradation depending on various parameters, such as oxygen, pH, metal-ion concentration (for example of iron or copper) or temperature. [H.-D. Belitz, W. Grosch, Lehrbuch der Lebensmittelchemie [Textbook of Food Chemistry], Springer-Verlag, 1987, 3rd Edition, p. 337.]

EP 0664290 describes derivatives of ascorbic acid in which the 2-position or also the 2- and 6-position is esterified by cinnamic acid. These ascorbic acid derivatives are used as antioxidants or, in accordance with EP 104631, as NO donors.

EP 0917871 discloses ascorbic acid derivatives whose hydroxyl group in the 4-position is substituted by $C_1$-$C_6$-alkoxycarbonyl and whose hydroxyl groups in the 5- and/or 6-position are substituted by $C_1$-$C_{20}$-acyl or $C_1$-$C_6$-alkoxycarbonyl, where the acyl chains are branched, unbranched, saturated or (poly)unsaturated, i.e. based on fatty acids. Aromatic systems are excluded. These compounds are also used as antioxidants EP 1527777 describes ascorbic acid derivatives in which at least one hydroxyl group of the ascorbic acid has been esterified by means of a benzoic acid, preferably a gallic acid. The compounds are described, inter alia, as inhibitors of tyrosine activity or as inhibitors of melanin synthesis. The use according to the invention for the functionalisation of matrices is not mentioned or even suggested.

G. Tschank et al, Biochem. J. 1994, 300, 75-79, describe the compounds $O^6$-(2-acetoxybenzoyl) L-ascorbate and $O^5O^6$-bis(2-acetoxybenzoyl) L-ascorbate. These compounds are capable of supporting the activity of the enzyme prolyl-4-hydroxylase, but the disubstituted compound has lower affinity to the enzyme.

Particularly suitable for the use according to the invention is at least one ascorbic acid derivative of the formula I

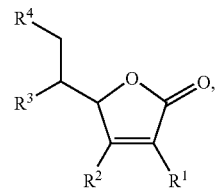

where
$R^1$ or $R^2$ each, independently of one another, denote hydroxyl, —O-alkyl, —OC(O)-alkyl, —OPO$_3$M or O-glycosyl,
alkyl denotes $C_1$-$C_6$-alkyl,
M denotes an alkali or alkaline-earth metal cation or H,
$R^3$ or $R^4$ each, independently of one another, denote hydroxyl or a radical B and
B denotes the radical of a pharmacological, antimicrobial, fungicidal, herbicidal, insecticidal or cosmetic active compound, of a UV filter, of an X-ray contrast agent or of a dye, with the proviso that at least one of the radicals $R^3$ or $R^4$ stands for a radical B.

$C_1$-$C_6$-alkyl denotes an alkyl group having 1, 2, 3, 4, 5 or 6 C atoms, for example methyl, ethyl, isopropyl, n-propyl, isobutyl, n-butyl, tert-butyl, n-pentyl or n-hexyl.

Alkoxy radicals which come into consideration for $R^1$ or $R^2$ are those whose alkyl group contains 1 to 6 C atoms, preferably 1 to 4 C atoms. Examples of alkoxy groups are methoxy, ethoxy, propoxy, isopropoxy, butoxy, isobutoxy or tert-butoxy.

The group —$OPO_3M$ is preferably the —$OPO_3H$ group, but it is also possible to employ salts of the formula I, where M in formula I corresponds to an alkali metal cation, for example of Na or K, or an alkaline-earth metal cation, for example of Mg or Ca.

The bonding of a carbohydrate in position 2 or 3 of the ascorbic acid, referred to as O-glycosyl in formula I, can take place, for example, for monosaccharides, such as ribose, arabinose xylose, lyxose, allose, altrose, glucose, mannose, gulose, idose, galactose, talose, ribulose, xylulose, psicose, fructose, sorbose or tagatose. This list covers both isomers, i.e. in each case the D or L forms.

Preference is given to the use of glucose, galactose or fructose, very particularly preferably glucose.

In principle, however, disaccharides, such as saccharose (or also known as sucrose), lactose, trehalose, maltose, cellobiose, gentiobiose or melibiose, are also suitable. This list covers both the □ and also the □ forms.

From the group of the disaccharides, preference is given to the use of saccharose or lactose, particularly preferably saccharose.

Preferably, the radical $R^1$ in formula I denotes hydroxyl and $R^2$ denotes —O-alkyl, —OC(O)-alkyl, —$OPO_3M$ or O-glycosyl, as described above.

Preferably, the radical $R^2$ in formula I denotes hydroxyl and $R^1$ denotes —O-alkyl, —OC(O)-alkyl, —$OPO_3M$ or O-glycosyl, as described above.

Particularly preferably, both radicals $R^2$ and $R^1$ are hydroxyl.

$R^3$ or $R^4$ are each, independently of one another, hydroxyl or a radical B and B is the radical of a pharmacological, antimicrobial, fungicidal, herbicidal, insecticidal or cosmetic active compound, of a UV filter, of an X-ray contrast agent or of a dye.

In a preferred embodiment, the radical $R^3$ is hydroxyl and $R^4$ corresponds to a radical B, as preferably described above and below.

However, it is also possible in accordance with the invention to employ mixtures of ascorbic acid derivatives of the formula I in which the radical B stands both for $R^3$ and $R^4$, and also for $R^3$ or $R^4$.

The radical B, as described in greater detail above and below, is preferably bonded to position 5 and/or 6 of the formula I via an ester function. The radical B is particularly preferably bonded via a carbonyloxy function. In a further embodiment, the radical B is bonded via an ether function.

The radicals $R^1$ and $R^2$ of the ascorbic acid derivatives of the formula I are selected in such a way that, on application to the matrix, in particular the skin, hair and/or nails, or also on application to isolated proteins or gelatine, bonds form to reactive groups of the matrix, such as amino and/or thiol groups. The bonding reaction is simplified if the ascorbic acid derivative of the formula I is activated by degradation through oxidation of the hydroxyl groups $R^1$ and/or $R^2$. The hydroxyl groups $R^1$ and/or $R^2$ can also form from an ascorbic acid derivative of the formula I where $R^1$ and/or $R^2 \neq H$ by hydrolysis on application to the matrix.

The theory of further functionalisation of the matrix is described below via bonding activation by ascorbic acid degradation, although functionalisation of the matrices is not intended to be tied to this theory.

In Scheme 1, the ascorbic acid derivative decomposes to give xylosone and/or 4-desoxypentosone, where, in the formulae of Scheme 1, $R^3$ denotes OH or a radical B and $R^4$ denotes a radical B, as described above:

Scheme 1:

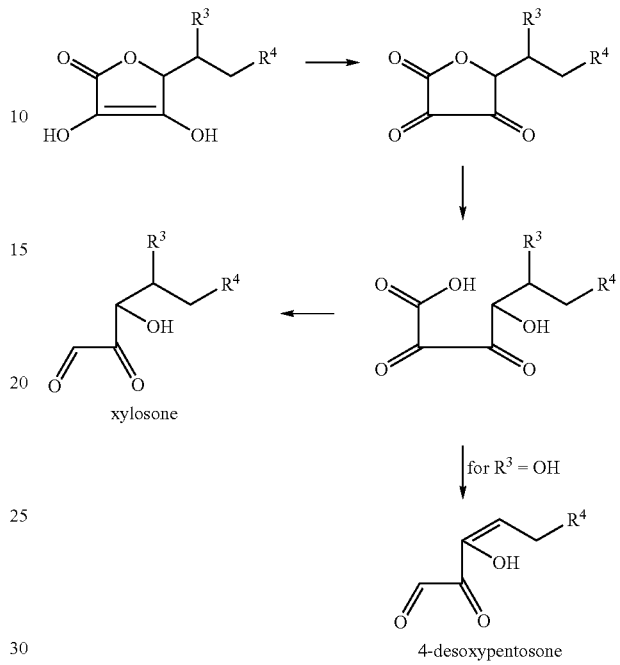

The reactive dicarbonyl compounds xylosone and 4-desoxypentosone are able to react with proteins and amino acids in the sense of a Maillard reaction. This step corresponds to integration of the active-compound-carrying radicals $R^3$ and/or $R^4$ into the matrix. The matrix is therefore functionalised corresponding to the active-compound radical.

Compared with, for example, non-bonding UV filters, this mechanism has two additional advantages, namely the antioxidative (degradation) reaction of the ascorbic acid skeleton and, where appropriate, a tanning reaction analogous to the Maillard reaction (self-tanning agent component).

In a variant of the invention, it is preferred for the radical B to be a radical of a pharmacological active compound.

The substances having a pharmacological action are preferably aromatic and contain a carbonyl function.

Examples of substances having a pharmacological action are:
1) Inflammation-inhibiting antirheumatics: for example those of the acetic acid derivatives, such as, for example, indomethacin (CAS: 53-86-1), acemetacin (CAS: 53164-05-9), tolmetin (CAS: 26171-23-3), diclofenac (CAS: 15307-86-5), lonozolac (CAS: 53808-88-1), and/or those of the propionic acid derivatives, such as, for example, ibuprofen (CAS: 15687-27-1), fenoprofen (CAS: 31879-05-7), sodium naproxen (CAS: 26159-34-2), ketoprofen (CAS: 22071-15-4);
2) Antiarteriosclerosis B vitamins: for example aluminium nicotinic acid (CAS: 1976-28-9), aminobenzoic acid (CAS: 150-13-0);
3) Antiarrythmic, anticonvulsant non-steroids, such as, for example, voltaren/diclofenac (CAS: 15307-86-5);
4) Antiarrythmic, beta-sympatholytic substances from class I, II, III and IV, such as, for example, BW-A-575-C (CAS: 103221-88-1);

5) β-Lactam antibiotics: for example those of the penam, crabapenem, oxapenam, cephem, oxacephem and monocyclic β-lactams, such as, for example, amoxillin (CAS: 26787-78-0), cefoxitin (CAS: 35607-66-0) and ampicillin (CAS: 69-53-4);
6) Antibiotics from the family of the penicillins, aminopenicillins, acylaminopenicillins, carboxypenicillins and cephalosporins, such as, for example, tazobactam (CAS: 89786-04-9), cloxacillin sulfone (CAS: 76788-83-5), sulbactam (CAS: 68373-14-8);
7) Antibiotics from the family of the tetracyclins, such as, for example, glycinmethyltetracyclin (CAS: 751-98-4), lymecyclin (CAS: 992-21-2), calcium chlorotetracyclin (CAS: 57122-99-3), apicyclin (CAS: 15599-51-6);
8) Inflammation-inhibiting prostaglandin antagonists, such as, for example, sodium lobenzarit (CAS: 64808-48-6), flutiazin (CAS: 7220-56-6), araprofen (CAS: 15250-13-2);
9) Antiseptic agents and antidiabetic agents from the family of the phenyl-sulfonamides, such as, for example, carboxytolbutamide (CAS: 2224-10-4);
10) Inflammation inhibitors, analgesics, collagenase inhibitors and keratolytic substances, such as, for example, salicylic acid (CAS: 69-72-7);
11) Antiasthmatics, for example those of the xanthin derivatives, such as, for example, acefyllin (CAS: 652-37-9);
12) Antiasthmatics and antianaphylactics, such as, for example, sodium ablukast (CAS: 96565-55-8), amlexanox (CAS: 68302-57-8), AH-7725 (CAS: 68302-57-8), calcium nedocromil (CAS: 101626-68-0);
13) Thyroid hormones and antiarteriosclerotic agents, such as, for example, detrothyronine (CAS: 5714-08-9), sodium levothyroxine (CAS: 55-03-8), sodium dextrothyroxine (CAS: 137-53-1);
14) Analgesics, inflammation inhibitors, antipyretics, for example those of the pyrazolidine derivatives, such as, for example, anthradione (CAS: 19854-90-1);
15) Chelating agents, such as, for example, HBED (CAS: 35998-29-9), calteridol (CAS: 132722-73-7);
16) Prostaglandins for ulcer therapy, such as, for example, sodium beraprost (CAS: 88475-69-8); or
17) cis- or trans-urocaninic acid.

These examples are intended to explain the possibilities by way of example without restricting the choice.

In a further variant of the invention, it is preferred for the radical B to be a radical of an antimicrobial active compound.

Particularly suitable here are preservatives which are carboxylic acid derivatives and in addition contain a conjugated π electron system, such as, for example, benzoic acid, p-hydroxybenzoic acid or sorbic acid.

These examples are intended to explain the possibilities by way of example without restricting the choice.

In a further variant of the invention, it is preferred for the radical B to be a radical of a fungicidal, herbicidal or insecticidal active compound. These substances can also be referred to in summary as pesticides.

The following suitable pesticides may be mentioned here by way of example:

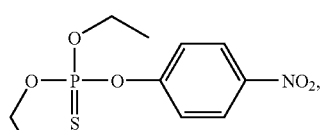

parathion(-ethyl)

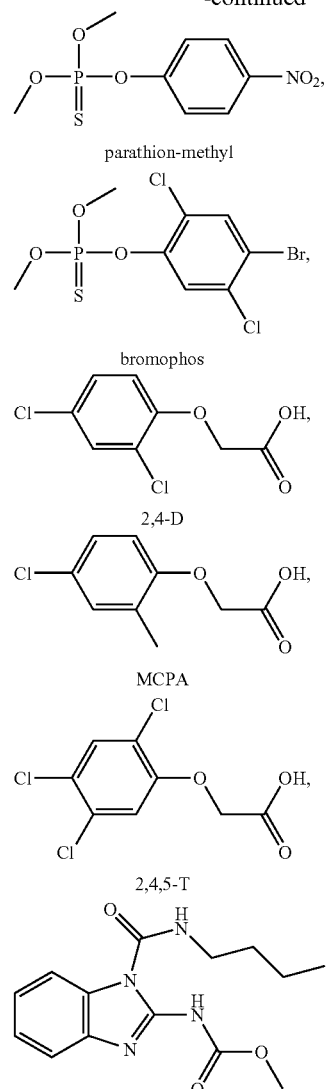

In a further variant of the invention, it is preferred for the radical B to be a radical of a cosmetic active compound.

Particularly suitable here are the substances nicotinic acid, nicotinamide, retinoic acid, biotin, i.e. containing the radical B=

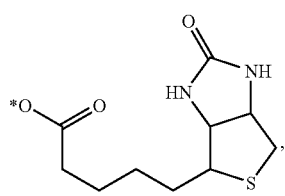

and the aromatic amino acids phenylalanine, tryptophan, histidine and tyrosine.

In a further variant of the invention, it is preferred for the radical B to be a radical of an X-ray contrast agent.

The X-ray contrast agents are preferably aromatic and contain a carbonyl function.

Examples of X-ray contrast agents are iocetaminic acid (CAS: 16034-77-8), iodocetylic acid (CAS: 54510-20-2), meglumin acetrizoate (CAS: 22154-43-4), iodohippurinic acid (CAS: 147-58-0), sodium bunamiodate (CAS: 1923-76-8), acetrizoic acid (CAS: 85-36-9), but also diagnostic agents for other applications, such as, for example, iocanlidinic acid (CAS: 74855-17-7), silver fluorescein (CAS: 25931-86-6), pankensan (CAS: 38219-60-2).

These examples are intended to explain by way of example the possibilities for bonded diagnostic substances, without restricting the choice.

In a further variant of the invention, it is preferred for the radical B to be a radical of a dye.

Preference is given to the use of organic dyes which are carboxylic acid derivatives. Mention is made by way of example of substances which serve for the colouring of foods, medicaments and cosmetics, such as
bixin (present in annatto, E160b, C.I. 75120); norbixin; apocarotinic acid ethyl ester, E160f, C.I. 40825; chlorophyll, E 140, C.I. 75810; erythrosine, E127, C.I. 45430; carmine, cochineal, E120, C.I. 75470; litholrubin BK, C.I. 15850:1; phloxin B, C.I. 45410; rhodamine B, C.I. 45170; red beet dye betanin, E162; tartrazine, E102, C.I. 19140; uranine, C.I. 45350 or fluorescein, C.I. 45350:1.

Further organic dyes which are carboxylic acid derivatives are given in "Gisbert Otterstätter: Die Färbung von Lebensmitteln, Arzneimitteln, Kosmetika [The Colouring of Foods, Medicaments, Cosmetics]; 2nd revised edition, Behr's Verlag Hamburg, 1995", or FD&C Yellow 5 (tartrazine), FD&C Yellow 6 (Sunset Yellow FCF), FD&C Yellow 10, FD&C Red 3 (erythrosine), FD&C Red 6 (litholrubin B), FD&C Red 7 (litholrubin BN), FD&C Red 21, FD&C Red 27, FD&C Red 28 (floxine B), FD&C Red 33, C.I. Natural Red 33, FD&C Red 36, FD&C Red 40, carmine, FD&C Blue 1 (Brilliant Blue FCF), C.I. Natural Green 3 (E141), FD&C Blue, FD&C Black 1 (Brilliant Black).

In general, the pharmacological, antimicrobial, fungicidal, herbicidal, insecticidal or cosmetic active compounds, dyes or X-ray contrast agents can also be taken to mean substances which are capable of absorbing UV radiation owing to their structure, so long as they have a conjugated π electron system of at least 4π electrons.

In a further variant of the invention, it is therefore also preferred for the radical B in formula I to be a substituent which absorbs UV radiation and has a conjugated π electron system of at least 4π electrons.

In a further variant of the invention, it is particularly preferred for the radical B in formula I to be a substituent which absorbs UV-A and/or UV-B radiation. These compounds also generally have a conjugated π electron system of at least 4π electrons. The radical B here is a UV filter, preferably a substituent of the formula II, III, IV, V, VI, VII, VIII, IX, X, XI and/or XII

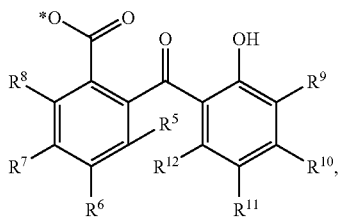

II

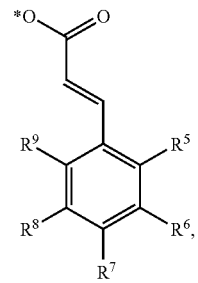

III

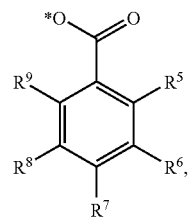

IV

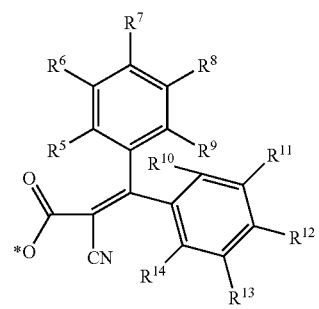

V

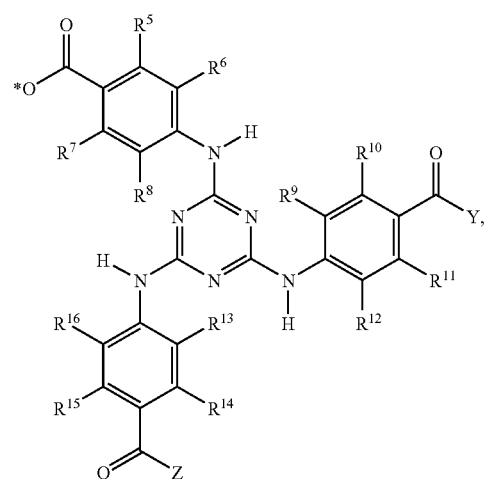

VI

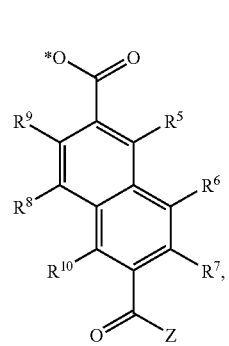

VII

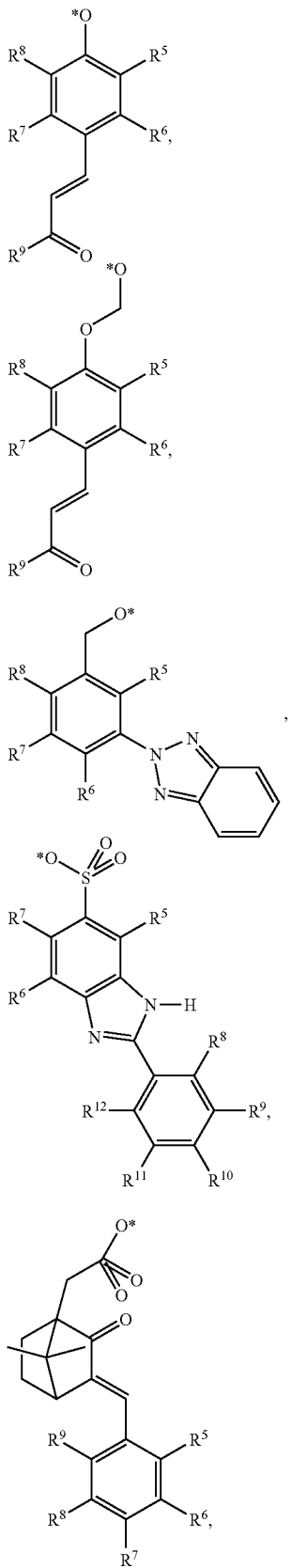

where
R[5] to R[16] each, independently of one another, denote H, —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl and A is alkyl having 1 to 4 C atoms, n is an integer from 1 to 25, X is the counterion to the cations [NHA$_2$]$^+$ and [NA$_3$]$^+$ or to the anion [SO$_3$]$^-$ and Y and Z are each, independently of one another, -ascorbyl, hydroxyl, —O-2-ethylhexyl, —O-hexyl, —OA or —NH—C(CH$_3$)$_3$.

In the formulae described above, A denotes alkyl having 1, 2, 3 or 4 C atoms, for example methyl, ethyl, propyl, isopropyl, n-butyl, isobutyl or tert-butyl. A is preferably methyl or ethyl, very particularly preferably ethyl.

n stands for an integer from 1 to 25, preferably for an integer 1, 2, 3, 4 or 5.

X describes the counterion for the cations [NHA$_2$]$^+$ and [NA$_3$]$^+$, where A has one of the meanings indicated above, preferably Cl$^-$, Br$^-$, I$^-$ or [SO$_4$]$^{2-}$, or the counterion of the anion [SO$_3$]$^-$, preferably an ammonium ion or an alkali metal or alkaline-earth metal cation, such as Na$^+$, K$^+$, Mg$^{2+}$ or Ca$^{2+}$.

However, it is also possible for partial charges in the molecule to be self-balanced, i.e. for compounds of the formula I to be in the form of a zwitter-ionic structure.

Compounds of the formula I can also be used in accordance with the invention as salts, i.e. at least one hydroxyl group of the ascorbic acid skeleton is in deprotonated form, and the charge is balanced by a countercation, for example an alkali or alkaline-earth metal cation.

For the substituents of the formula II, the radicals R[5] to R[9], R[11] and R[12] are preferably H and R[10] is —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

R[10] in formula II is preferably —OA, —NH$_2$, —NHA or —NA$_2$, very particularly preferably —OA or —NA$_2$, where A has one of the meanings indicated above.

For the substituents of the formula III, the radicals R[5], R[6], R[8] and R[9] are preferably H and R[7] is —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

R[7] in formula III is preferably —OA, —NH$_2$, —NHA or —NA$_2$, very particularly preferably —OA or —NA$_2$, where A has one of the meanings indicated above.

For the substituents of the formula IV, the radicals R[5], R[6], R[8] and R[9] are preferably H and R[7] is —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

R[7] in formula IV is preferably —OA, —NH$_2$, —NHA or —NA$_2$, very particularly preferably —OA or —NA$_2$, where A has one of the meanings indicated above.

For the substituents of the formula IV, the radicals R[5], R[8] and R[9] are alternatively preferably H, R[6] denotes 2H-benzotriazol-2-yl and R[7] is —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H or —[SO$_3$]X. In this substituent arrangement, R[7] is particularly preferably OH.

For the substituents of the formula V, the radicals $R^6$, $R^8$, $R^{11}$ and $R^{13}$ are preferably H and the substituents $R^5$, $R^7$, $R^9$, $R^{10}$, $R^{12}$ and $R^{14}$ are each, independently of one another, H, —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

$R^5$, $R^7$, $R^9$, $R^{10}$, $R^{12}$ and $R^{14}$ in formula V are each, independently of one another, preferably H, —OA, —NH$_2$, —NHA or —NA$_2$, very particularly preferably H, where A has one of the meanings indicated above.

For the substituents of the formula VI, the radicals $R^6$, $R^8$, $R^9$, $R^{12}$, $R^{13}$ and $R^{16}$ are preferably H and the substituents $R^5$, $R^7$, $R^{10}$, $R^{14}$ and $R^{15}$ are each, independently of one another, H, —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

$R^5$, $R^7$, $R^{10}$, $R^{11}$, $R^{14}$ and $R^{15}$ in formula VI are each, independently of one another, preferably H, —OA, —NH$_2$, —NHA or —NA$_2$, very particularly preferably H, where A has one of the meanings indicated above.

For the substituents of the formula VII, the radicals $R^5$, $R^6$, $R^7$, $R^8$, $R^9$ and $R^{10}$ are preferably H and Z denotes -ascorbyl, hydroxyl, —O-2-ethylhexyl, —O-hexyl, —OA or —NH—C(CH$_3$)$_3$.

Z in formula VII particularly preferably denotes OH.

For the substituents of the formula VIII, the radicals $R^5$, $R^6$, $R^7$ and $R^8$ are preferably H and the substituent $R^9$ is preferably —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

$R^9$ in formula VIII particularly preferably denotes —OA.

For the substituents of the formula IX, the radicals $R^5$, $R^6$, $R^7$ and $R^8$ are preferably H and the substituent $R^9$ is preferably —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

$R^9$ in formula IX particularly preferably denotes —OA.

For the substituents of the formula X, the radicals $R^5$, $R^7$ and $R^8$ are preferably H and the substituent $R^6$ is preferably —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

$R^6$ in formula X particularly preferably denotes —OH.

For the substituents of the formula XI, the radicals $R^5$, $R^6$, $R^7$, $R^8$, $R^9$, $R^{11}$ and $R^{12}$ are preferably H and the substituent $R^{10}$ is preferably H, —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

$R^{10}$ in formula XI particularly preferably denotes H.

For the substituents of the formula XII, the radicals $R^5$, $R^6$, $R^8$ and $R^9$ are preferably H and the substituent $R^7$ is preferably —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

$R^7$ in formula XII particularly preferably denotes A. In a particular variant, compounds of the formula XII which contain the moiety

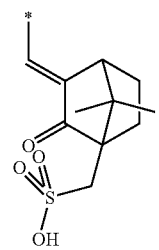

as substituent $R^7$ are also suitable.

Further preferred combinations are disclosed in the claims.

Particularly preferred embodiments of the radical B can be seen in the following moieties:

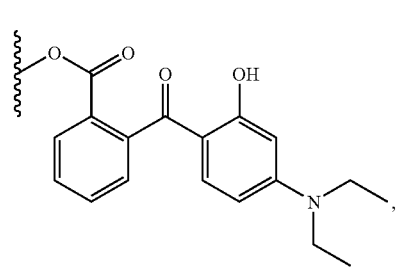

IIa

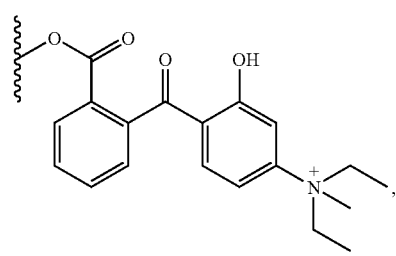

IIb

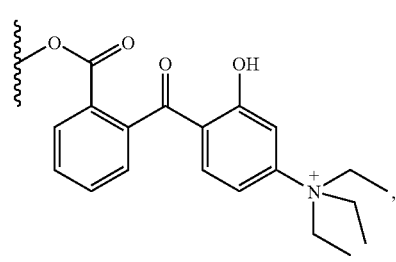

IIc

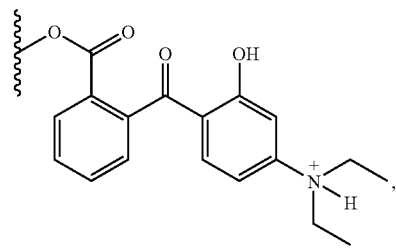

IId

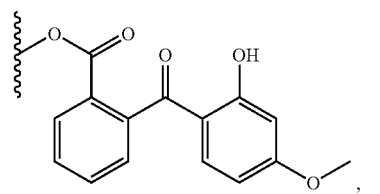

IIe

-continued
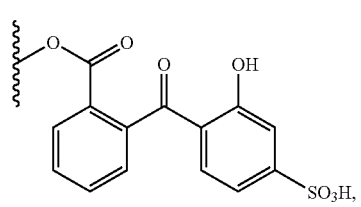  IIf
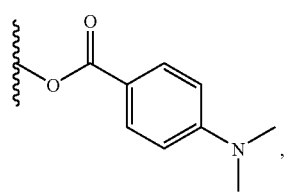  IVa
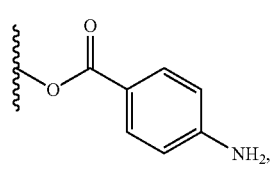  IVb
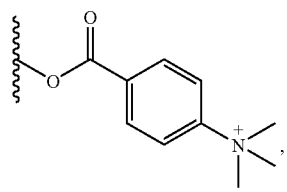  IVc
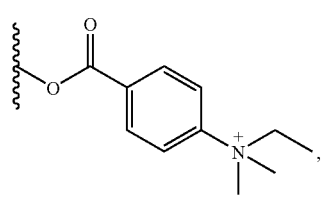  IVd
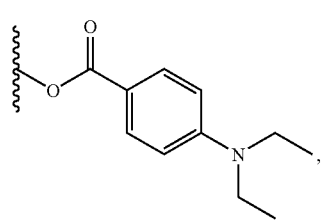  IVe
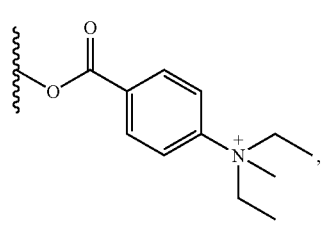  IVf
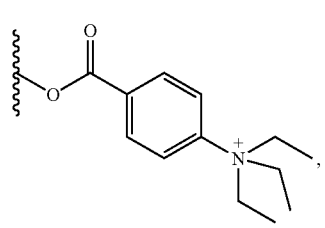  IVg
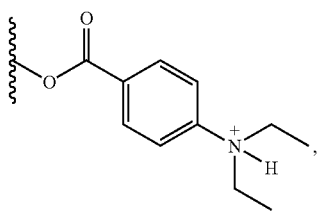  IVh
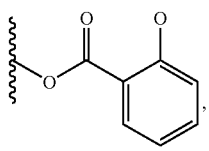  IVi
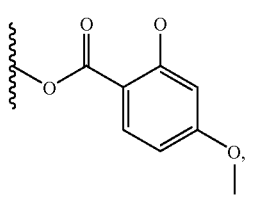  IVj
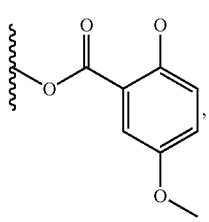  IVk
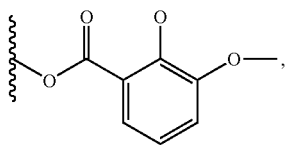  IVm
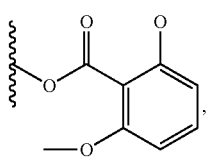  IVn
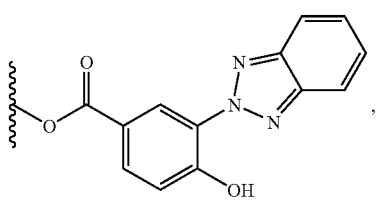  IVo
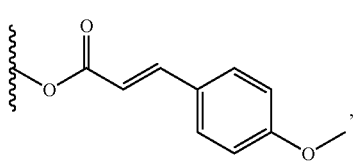  IIIa

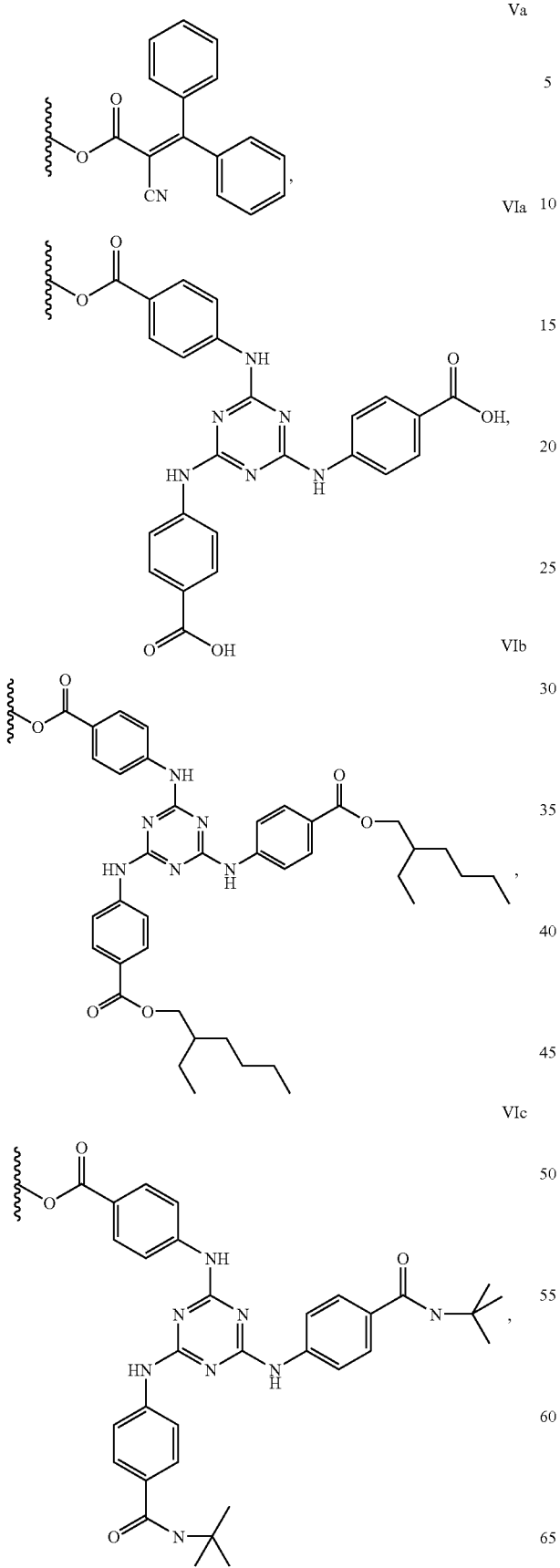

-continued

IXa 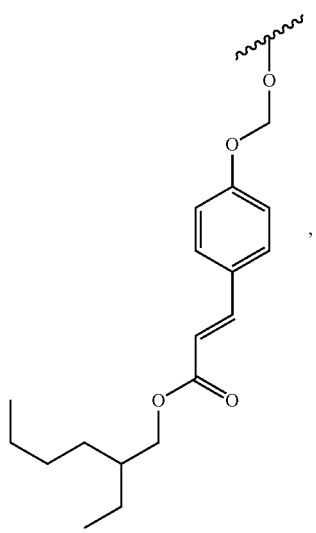

IXb 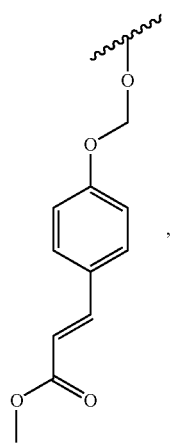

Xa 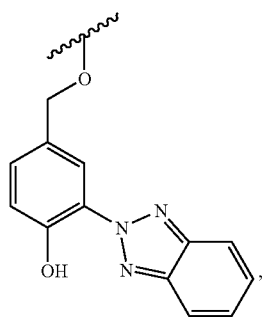

XIa 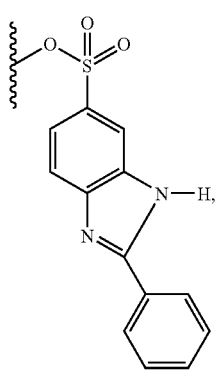

XIIa 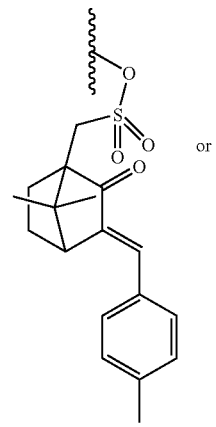

or

XIIb 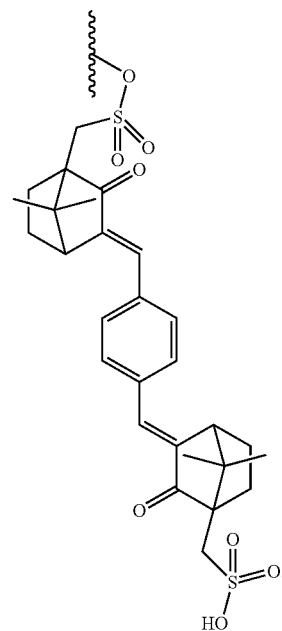

The invention also relates to the compounds of the formula I

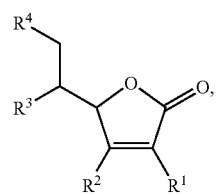

I where
$R^1$ or $R^2$ are each, independently of one another, hydroxyl, —O-alkyl, —OC(O)-alkyl, —OPO$_3$M or O-glycosyl,
alkyl is $C_1$-$C_6$-alkyl,
M is an alkali or alkaline-earth metal cation or H,
$R^3$ or $R^4$ are each, independently of one another, hydroxyl or a radical B and
B is a substituent of the formula II, III, IV, V, VI, VII, VIII, IX, X, XI and/or XII

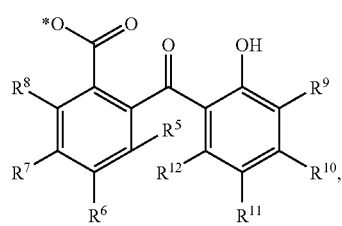
II
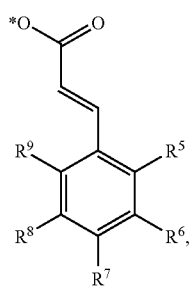
III
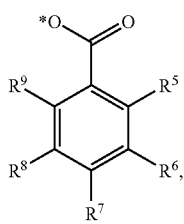
IV
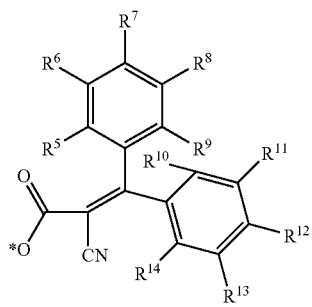
V
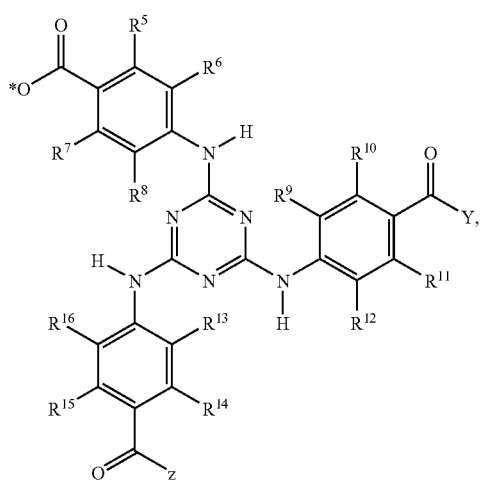
VI
-continued
VII
VIII
IX
X
XI -continued

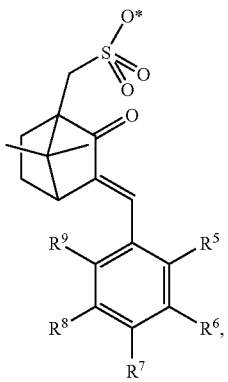

XII where
R$^5$ to R$^{16}$ each, independently of one another, denote H, —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl and A is alkyl having 1 to 4 C atoms, n is an integer from 1 to 25, X is the counterion to the cations [NHA$_2$]$^+$ and [NA$_3$]$^+$ or to the anion [SO$_3$]$^-$ and Y and Z are each, independently of one another, -ascorbyl, hydroxyl, —O-2-ethylhexyl, —O-hexyl, —OA or —NH—C(CH$_3$)$_3$, where for R$^5$ to R$^9$ in formula IV, the radicals H, OH and OA are excluded, apart from the case where at least one substituent from R$^5$ to R$^9$ denotes A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl and with the proviso that at least one of the radicals R$^3$ or R$^4$ stands for a radical B.

A, n and X have a meaning as described above.

In a variant of the invention, preference is given to compounds of the formula I if R$^2$ in formula I denotes hydroxyl.

In a variant of the invention, preference is given to compounds of the formula I if R$^1$ in formula I denotes hydroxyl.

In a variant of the invention, preference is given to compounds of the formula I if the radicals R$^5$ to R$^9$, R$^{11}$ and R$^{12}$ in formula II are preferably H and R$^{10}$ is —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

R$^{10}$ in formula II is preferably —OA, —NH$_2$, —NHA or —NA$_2$, very particularly preferably —OA or —NA$_2$, where A has one of the meanings indicated above.

In a variant of the invention, preference is given to compounds of the formula I if the radicals R$^5$, R$^6$, R$^8$ and R$^9$ in formula III are preferably H and R$^7$ is —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

R$^7$ in formula III is preferably —OA, —NH$_2$, —NHA or —NA$_2$, very particularly preferably —OA or —NA$_2$, where A has one of the meanings indicated above.

In a variant of the invention, preference is given to compounds of the formula I if the radicals R$^5$, R$^6$, R$^8$ and R$^9$ in the formula IV are preferably H and R$^7$ is -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

R$^7$ in formula IV is preferably —NH$_2$, —NHA, —NA$_2$, —[NHA$_2$]X or —[NA$_3$]X, very particularly preferably —NA$_2$, where A has one of the meanings indicated above.

In a variant of the invention, preference is given to compounds of the formula I if the radicals R$^5$, R$^8$ and R$^9$ in the formula IV are preferably H, R$^6$ denotes 2H-benzotriazol-2-yl and R$^7$ denotes —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl. R$^7$ in this variant of the invention is very particularly preferably —OH.

In a variant of the invention, preference is given to compounds of the formula I if the radicals R$^6$, R$^8$, R$^{11}$ and R$^{13}$ in the formula V are preferably H and the substituents R$^5$, R$^7$, R$^9$, R$^{10}$, R$^{12}$ and R$^{14}$ in the formula V are each, independently of one another, H, —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

R$^5$, R$^7$, R$^9$, R$^{10}$, R$^{12}$ and R$^{14}$ in formula V are each, independently of one another, preferably H, —OA, —NH$_2$, —NHA or —NA$_2$, very particularly preferably H, where A has one of the meanings indicated above.

In a variant of the invention, preference is given to compounds of the formula I if the radicals R$^6$, R$^8$, R$^9$, R$^{12}$, R$^{13}$ and R$^{16}$ of the formula VI are preferably H, the substituents R$^5$, R$^7$, R$^{10}$, R$^{11}$, R$^{14}$ and R$^{15}$ are each, independently of one another, H, —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl, and Z is hydroxyl, —O-2-ethylhexyl, OA or —NH—C(CH$_3$)$_3$.

R$^5$, R$^7$, R$^{10}$, R$^{11}$, R$^{14}$ and R$^{15}$ in formula VI are each, independently of one another, preferably H, —OA, —NH$_2$, —NHA or —NA$_2$, very particularly preferably H, where A has one of the meanings indicated above. Z in formula VI is particularly preferably hydroxyl, —O-2-ethylhexyl or —NH—C(CH$_3$)$_3$.

In a variant of the invention, preference is given to compounds of the formula I if the radicals R$^5$, R$^6$, R$^7$, R$^8$, R$^9$ and R$^{10}$ in the formula VII are H and Z denotes -ascorbyl, hydroxyl, —O-2-ethylhexyl, —O-hexyl, —OA or —NH—C(CH$_3$)$_3$. Z is very particularly preferably —OH.

In a variant of the invention, preference is given to compounds of the formula I if the radicals R$^5$, R$^6$, R$^7$ and R$^8$ in formula VIII are H and R$^9$ denotes —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl. R$^9$ in formula VIII is particularly preferably A or 2-ethylhexyl.

In a variant of the invention, preference is given to compounds of the formula I if the radicals R$^5$, R$^6$, R$^7$ and R$^8$ in formula IX are H and R$^9$ denotes —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl. R$^9$ in formula IX is particularly preferably A or 2-ethylhexyl.

In a variant of the invention, preference is given to compounds of the formula I if the radicals R$^5$, R$^7$ and R$^8$ in formula X are H and R$^6$ denotes —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl. R$^6$ in formula X is particularly preferably —OH.

In a variant of the invention, preference is given to compounds of the formula I if the radicals R$^5$, R$^6$, R$^7$, R$^8$, R$^9$, R$^{11}$ and R$^{12}$ in formula XI are H and R$^{10}$ denotes H, —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl. R$^{10}$ in formula XI is particularly preferably H.

In a variant of the invention, preference is given to compounds of the formula I if the radicals R$^5$, R$^6$, R$^8$ and R$^9$ in formula XII are H and R$^7$ denotes —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl. R$^7$ in formula XII is particularly preferably A.

Further preferred combinations are disclosed in the claims.

Particularly preferred embodiments of compounds of the formula I can be seen in moieties IIa-IIf, IIIa, IVa-IVo, Va VIa-VIc, VIIa-VIIb, VIIIa-VIIIb, IXa-IXb, Xa, XIa and/or XIIa-XIIb for the radical B, as described above.

The compounds of the formula I, as described above, can generally be prepared by methods known per se to the person skilled in the art from the literature. The reaction conditions for esterifications or etherifications are standard prior art, and the choice of suitable reaction conditions is part of the standard expert knowledge of the person skilled in the art of synthesis.

The invention likewise relates to a process for the preparation of compounds of the formula I, as described above, where the meaning of sub-formulae XI and XII is excluded for the radical B, characterised in that
a) a compound of the formula XIII

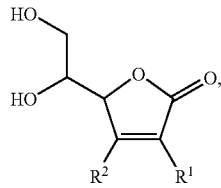

XIII in which
R$^1$ or R$^2$ has one of the meanings indicated above for the formula I or indicated as preferred,
is reacted directly with a compound of the formula XIV

B-M                                XIV in which B can have one of the meanings described above, where the sub-formulae XI and XII are excluded, and
M denotes an alkali metal or alkaline-earth metal cation or H, or
b) the hydroxyl groups of the compound of the formula XIII, as described above, are protected to give a compound of the formula XV

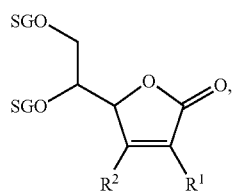

XV in which
R$^1$ or R$^2$ has one of the meanings described above for the formula I and SG denotes a protecting group, in a subsequent step the radicals R$^1$ and/or R$^2$, if these are hydroxyl groups, are protected by a second protecting group which can be cleaved off again under different reaction conditions to the protecting group SG,
the protecting groups SG of the compounds of the formula XV are cleaved off again, and the resultant compound is reacted with a compound of the formula XIV

B-M                                XIV, where B has a meaning described above for the formula I, where sub-formulae XI and XII are excluded, and
M denotes an alkali metal or alkaline-earth metal cation or H, and the radicals R$^1$ and/or R$^2$ for the hydroxyl group are subsequently deprotected, and these hydroxyl groups are, if desired, converted into another radical R$^1$ or R$^2$≠OH, as described above.

The direct esterification of the compounds of the formula XIII using compounds of the formula XIV, if these are bonded via a carbonyloxy function, is carried out in the presence of concentrated sulfuric acid and preferably under inert-gas conditions. The mixture of the components is advantageously prepared at temperatures <5° C. The actual reaction temperature is between 10 and 60° C., preferably between 15 and 30° C. The reaction is particularly preferably carried out at room temperature.

Some of the starting materials of the formulae XIII and XIV are commercially available, for example ascorbic acid, ascorbic acid phosphate, sodium and magnesium ascorbyl phosphate, ascorbic acid glucoside, salicylic acid, p-methoxycinnamic acid, p-hydroxycinnamic acid, 2-(4-diethylamino-2-hydroxybenzoyl)benzoic acid or 2-(4-methoxy-2-hydroxybenzoyl)benzoic acid, or can be synthesised by methods which are described, for example, in the standard works, such as Houben-Weyl, Methoden der organischen Chemie [Methods of Organic Chemistry], Georg-Thieme-Verlag, Stuttgart, to be precise under reaction conditions which are known and suitable for the said reactions. Use can also be made here of variants known per se which are not mentioned here in greater detail.

In the case of direct esterification, a mixture of ascorbic acid C-6 esters and ascorbic acid C-5 esters forms as a consequence of the synthesis, where the ascorbic acid C-6 ester generally predominates. Ascorbic acid C-6 esters are compounds of the formula I in which R$^4$ denotes B. Ascorbic acid C-5 esters are compounds of the formula I in which R$^3$ denotes B. These mixtures can of course be separated by methods which are known to the person skilled in the art.

Ether formation by reaction of compounds of the formula XIV in which B corresponds to the sub-formulae VIII, IX or X and in which M=H with compounds of the formula XIII is preferably carried out in the presence of triphenylphosphine and diisopropyl azodicarboxylate, in an inert solvent, for example a halogenated hydrocarbon, such as dichloromethane, an ether, such as tetrahydrofuran or dioxane, an amide, such as DMF or dimethyl-acetamide, a nitrile, such as acetonitrile, in dimethyl sulfoxide or in the presence of these solvents, at temperatures between about −10 and 40, preferably between 0 and 30°. Depending on the conditions used, the reaction time is between a few minutes and several days.

If the synthesis of the compounds of the formula I in which B corresponds to one of the moieties VIII, IX or X is carried out using starting compounds of the formula XVIII B'-Hal                              XVIII, where Hal denotes Cl, Br or I and
B' corresponds to the sub-formula VIII', IX' or X', where all substituents have a meaning indicated above,

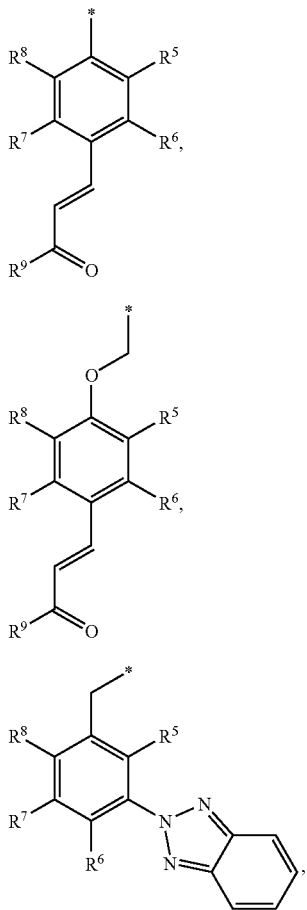

a classical nucleophilic substitution takes place. The corresponding protecting-group chemistry, as described below, should be used here. The reaction conditions of a nucleophilic substitution are adequately known to the person skilled in the art of synthesis.

The alternative preparation of the compounds according to the invention is essentially based on protecting-group chemistry of the hydroxyl groups of the compounds of the formula XIII, as defined above, in order that the esterification can take place specifically in position 5 and/or 6 of the ascorbic acid skeleton. However, the esterification using compounds of the formula XIV can also be carried out without prior protecting-group chemistry, where the reaction conditions are adequately known to the person skilled in the art.

The protecting groups are generally selected to be different from one another so that they can be cleaved off selectively (cf. in this respect: T. W. Greene, P. G. M. Wuts, Protective Groups in Organic Chemistry, 2nd Edn., Wiley, New York 1991 or P. J. Kocienski, Protecting Groups, 1st Edn., Georg Thieme Verlag, Stuttgart-New-York, 1994, H. Kunz, H. Waldmann in Comprehensive Organic Synthesis, Vol. 6 (eds. B. M. Trost, I. Fleming, E. Winterfeldt), Pergamon, Oxford, 1991, pp. 631-701).

The expression "hydroxyl-protecting group" is likewise known in general terms and relates to groups which are suitable for protecting a hydroxyl group against chemical reactions. Typical of such groups are unsubstituted or substituted aryl, aralkyl, aroyl or acyl groups, furthermore also alkyl groups, alkyl-, aryl- or aralkylsilyl groups or O,O- or O,S-acetals. The nature and size of the hydroxyl-protecting groups is not crucial since they are removed again after the desired chemical reaction or reaction sequence; preference is given to groups having 1-20, in particular 1-10, C atoms. Examples of hydroxyl-protecting groups are, inter alia, aralkyl groups, such as benzyl, 4-methoxybenzyl or 2,4-dimethoxybenzyl, aroyl groups, such as benzoyl or p-nitrobenzoyl, acyl groups, such as acetyl or pivaloyl, p-toluenesulfonyl, alkyl groups, such as methyl or tert-butyl, but also allyl, alkyl-silyl groups, such as trimethylsilyl (TMS), triisopropylsilyl (TIPS), tert-butyl-dimethylsilyl (TBS) or triethylsilyl, trimethylsilyl-ethyl, aralkylsilyl groups, such as tert-butyldiphenylsilyl (TBDPS), cyclic acetals, such as isopropylidene, cyclopentylidene, cyclohexylidene, benzylidene, p-methoxybenzylidene or o,p-dimethoxybenzylidene acetal, acyclic acetals, such as tetrahydropyranyl (Thp), methoxymethyl (MOM), methoxyethoxymethyl (MEM), benzyloxymethyl (BOM) or methylthiomethyl (MTM). Particularly preferred hydroxyl-protecting groups are benzyl, acetyl, tert-butyl or TBS.

The starting material employed for the synthesis is preferably ascorbic acid whose hydroxyl groups in the 5- and 6-position are protected by protecting groups SG, as described above, by known methods to give compounds of the formula XV. A cyclic protecting group which simultaneously effectively protects both positions 5 and 6 is advantageously selected. Examples of compounds of the formula XV are accordingly 5,6-isopropylidene, cyclopentylidene, cyclohexylidene, benzylidene, p-methoxybenzylidene or o,p-dimethoxybenzylidene ascorbate. 5,6-Isopropylidene ascorbate is preferably employed.

The hydroxyl groups in positions 2 and 3 are subsequently protected with the aid of protecting groups, as described above, where an aralkyl group or an alkylsilyl group is advantageously selected, particularly preferably an aralkyl group, for example the benzyl group.

After liberation of the hydroxyl groups protected in the first step, a reaction is carried out with a compound of the formula XIV, where B and M have a meaning described above, or with compounds of the formula XVIII.

If a reaction is carried out with a compound of the formula XIV in which M=H and B preferably corresponds to a sub-formula II, III, IV, V, VI or VII, the coupling reaction is preferably carried out in the presence of a dehydrating agent, for example a carbodiimide, such as dicyclohexylcarbodiimide (DCC), N-(3-dimethylaminopropyl)-N'-ethylcarbodiimide hydrochloride (EDC) or diisopropylcarbodiimide (DIC), furthermore, for example, propanephosphonic anhydride (cf. Angew. Chem. 1980, 92, 129), diphenyl-phosphoryl azide or 2-ethoxy-N-ethoxycarbonyl-1,2-dihydroquinoline, in an inert solvent, for example a halogenated hydrocarbon, such as dichloro-methane, an ether, such as tetrahydrofuran or dioxane, an amide, such as DMF or dimethylacetamide, a nitrile, such as acetonitrile, in dimethyl sulfoxide or in the presence of these solvents, at temperatures between about −10 and 40, preferably between 0 and 30°. Depending on the conditions used, the reaction time is between a few minutes and several days.

Instead of compounds of the formula XIV, as defined above, it is also possible to employ derivatives of the formula XIV, preferably a pre-activated carboxylic acid or a carboxylic acid halide, a symmetrical or mixed anhydride or an active ester. Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart). Activated esters are advantageously formed in situ, for example by addition of HOBt (1-hydroxybenzotriazole) or N-hydroxysuccinimide.

The reaction is generally carried out in an inert solvent, on use of a halide of the formula XIV in the presence of an acid-binding agent, preferably an organic base, such as triethylamine, dimethylaniline, pyridine, dimethyl-aminopyridine or quinoline.

The addition of an alkali or alkaline-earth metal hydroxide, carbonate or bicarbonate or of another salt of a weak acid of the alkali or alkaline-earth metals, preferably of potassium, sodium, calcium or caesium, may also be favourable.

After coupling and thus introduction of the active-compound-providing radical into the skeleton of ascorbic acid is complete, the hydroxyl groups in positions 2 and 3 are deprotected, giving compounds of the formula I in which $R^1$ and $R^2$ denote hydroxyl. The conversion of these hydroxyl groups, if desired, into other radicals $R^1$ and $R^2$, as defined above, is carried out by standard methods, for example etherification, esterification or glycosylation.

By changing the reaction conditions or generally the esterification method, it is also possible to modify the synthesis of the current secondary component, the ascorbic acid C-5 ester (specifically for Example 1-(R)-1-((R)-3,4-dihydroxy-5-oxo-2,5-dihydrofuran-2-yl)-2-hydroxyethyl (4-diethylamino-2-hydroxybenzoyl)benzoate), in such a way that this product forms the principal component and the ascorbic acid C-6 ester (specifically for Example 1 (R)-2-((R)-3,4-dihydroxy-5-oxo-2,5-dihydrofuran-2-yl)-2-hydroxyethyl 2-(4-diethylamino-2-hydroxybenzoyl)benzoate) is formed in an amount of 0 to 25%. Suitable esterification methods here are, for example, enzymatic esterifications.

The invention also relates to a process for the preparation of compounds of the formula I in which the radical B corresponds to the moieties of the formula XI and/or XII, characterised in that a) a compound of the formula XIII

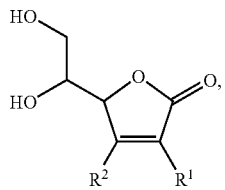

XIII in which $R^1$ or $R^2$ have one of the meanings described above for the formula I, is reacted with a compound of the formula XVI or XVII

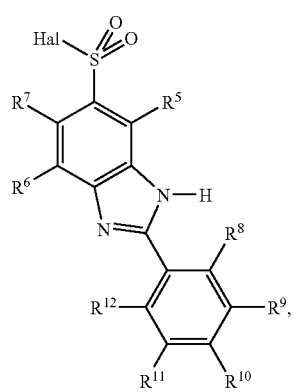

XVI

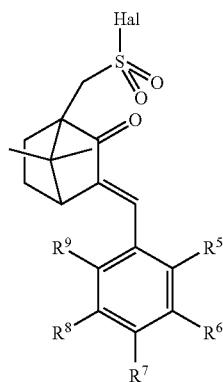

XVII in which $R^5$ to $R^{12}$ have one of the meanings described above for the formula I and Hal denotes Cl, Br, I or active ester, b) the hydroxyl groups of the compound of the formula XIII, as described above, are protected to give a compound of the formula XV

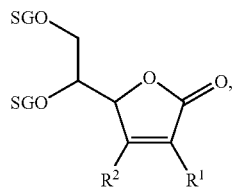

XV in which $R^1$ or $R^2$ have one of the meanings described above for the formula I, the radicals $R^1$ and/or $R^2$, if these are hydroxyl groups, are subsequently protected by a second protecting group which can be cleaved off again under different reaction conditions to the protecting group SG, the protecting groups SG of the compounds of the formula XV are cleaved off again, and the resultant compound is reacted with a compound of the formula XVI or XVII

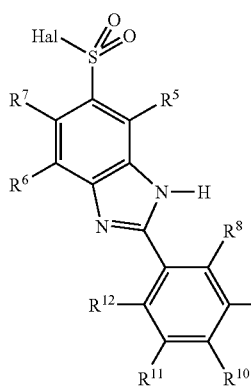

XVI

-continued

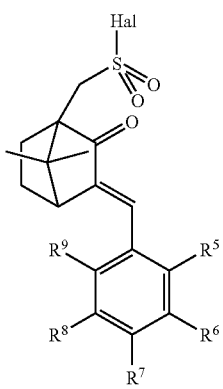

XVII in which $R^5$ to $R^{12}$ have one of the meanings described above for the formula I and Hal denotes Cl, Br, I or active ester, and the radicals $R^1$ and/or $R^2$ are subsequently deprotected as hydroxyl group, and these hydroxyl groups are, if desired, converted into another radical $R^1$ or $R^2 \neq OH$ as described above.

In the formulae XVI or XVII, Hal preferably denotes Cl, Br or I, particularly preferably Cl or Br, very particularly preferably Cl.

The reaction of the compounds of the formula XIII with compounds of the formula XVI or XVII is generally carried out in an inert solvent, in the presence of an acid-binding agent, preferably an organic base, such as triethylamine, dimethylaniline, pyridine, dimethylaminopyridine or quinoline.

The addition of an alkali or alkaline-earth metal hydroxide, carbonate or bicarbonate or of another salt of a weak acid of the alkali or alkaline-earth metals, preferably of potassium, sodium, calcium or caesium, may also be favourable.

The reaction here can of course also be carried out via the classical protecting-group strategy or chemistry, as described above. The comments and steps as described above also apply to this reaction according to the invention.

The ascorbic acid derivatives described are able to bond to textiles or textile fibres and thus to develop their action in each case depending on the radical B, for example UV protection, protection against oxidation, or they also serve for impregnation. Undesired material damage is thus reduced.

The ascorbic acid derivatives according to the invention in which the radical B is a substituent which absorbs UV radiation and has a conjugated π electron system of at least 4π electrons, preferably the UVA-, UV-B- or UV(A+B)-absorbing UV filters or the moieties of the formulae II, III, IV, V, VI, VII, VIII, IX, X, XI and/or XII, also have, for example, antiageing effects and have the advantages for the skin derived from ascorbic acid, i.e. they serve, for example, for skin regeneration and cause wrinkle reduction of (light)-aged skin, they furthermore increase, for example, the skin relief density or strengthen, for example, the dermis-epidermis bond (papilla index). They protect the skin against UV-induced damage or they have, for example, a skin-bleaching action. They have, for example, an antibacterial action, i.e. they can reduce sweat odour or improve the skin appearance in the case of skin impurities and/or acne.

The ascorbic acid derivatives according to the invention in which the radical B is a substituent which absorbs UV radiation and has a conjugated π electron system of at least 4π electrons, preferably the UVA-, UV-B- or UV(A+B)-absorbing UV filters or the moieties of the formulae II, III, IV, V, VI, VII, VIII, IX, X, XI and/or XII, are able to bond to hair and can thus suppress the hair damage caused by UV light or by oxidation, in particular with respect to colour and morphology. For example, protection can thus be provided against bleaching of the hair.

The ascorbic acid derivatives according to the invention in which the radical B is a substituent which absorbs UV radiation and has a conjugated π electron system of at least 4π electrons, preferably the UVA-, UV-B- or UV(A+B)-absorbing UV filters or the moieties of the formulae II, III, IV, V, VI, VII, VIII, IX, X, XI and/or XII, are able to bond not only to nitrogen-containing, but also to sulfur-containing hair functionalities, such as, for example, to thiolic groups. Owing to the good reduction properties of the compounds, the ascorbic acid derivatives according to the invention can be employed, for example through controlled reduction of disulfide bridges, in hair-treatment products for defrizzing or for the formation of permanent waves.

EP 1728501 describes the use of UVA light-protection filters which are bonded to a polypeptide. Analogously to the teaching of EP 1728501, the ascorbic acid derivatives according to the invention in which the radical B is a substituent which absorbs UV radiation and has a conjugated π electron system of at least 4π electrons, preferably the UVA-, UV-B- or UV(A+B)-absorbing UV filters or the moieties of the formulae II, III, IV, V, VI, VII, VIII, IX, X, XI and/or XII, can be combined with an amino acid, peptide or protein or bonded to an amino acid, peptide or protein before application.

Corresponding to the preferred use of the compounds according to the invention for the functionalisation of matrices, the present invention furthermore relates to an agent, for example a cosmetic, dermatological or pharmaceutical composition, comprising at least one compound of the formula I

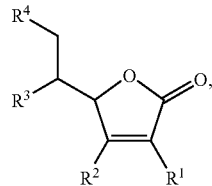

I where $R^1$ or $R^2$ each, independently of one another, denote hydroxyl, —O-alkyl, —OC(O)-alkyl, —OPO$_3$M or O-glycosyl, alkyl is $C_1$-$C_6$-alkyl, M is an alkali or alkaline-earth metal cation or H, $R^3$ or $R^4$ are each, independently of one another, hydroxyl or a radical B and B is the radical of a pharmacological, fungicidal, herbicidal, insecticidal or cosmetic active compound, of an X-ray contrast agent or of a dye or is a substituent of the formula II, III, IV, V, VI, VII, VIII, IX, X, XI and/or XII

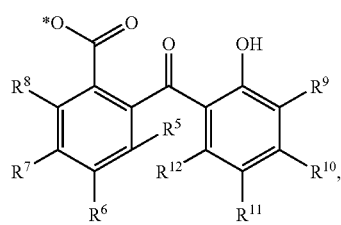

II

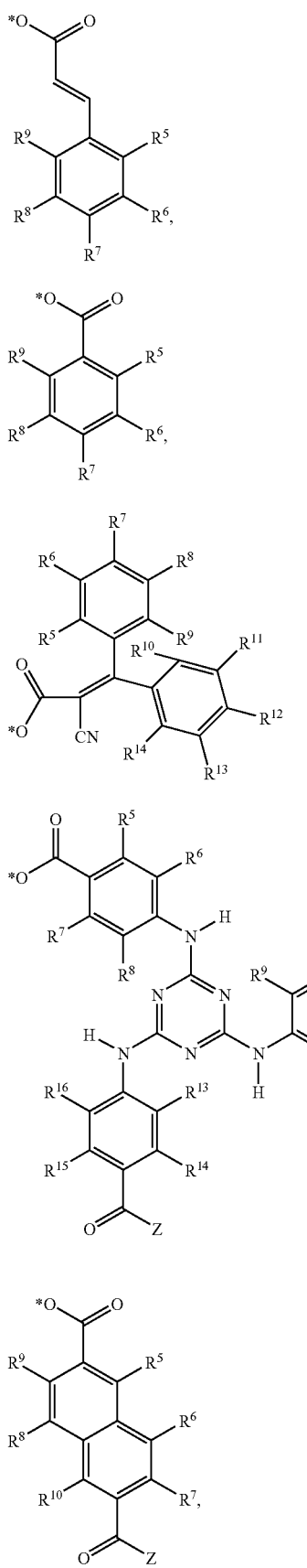
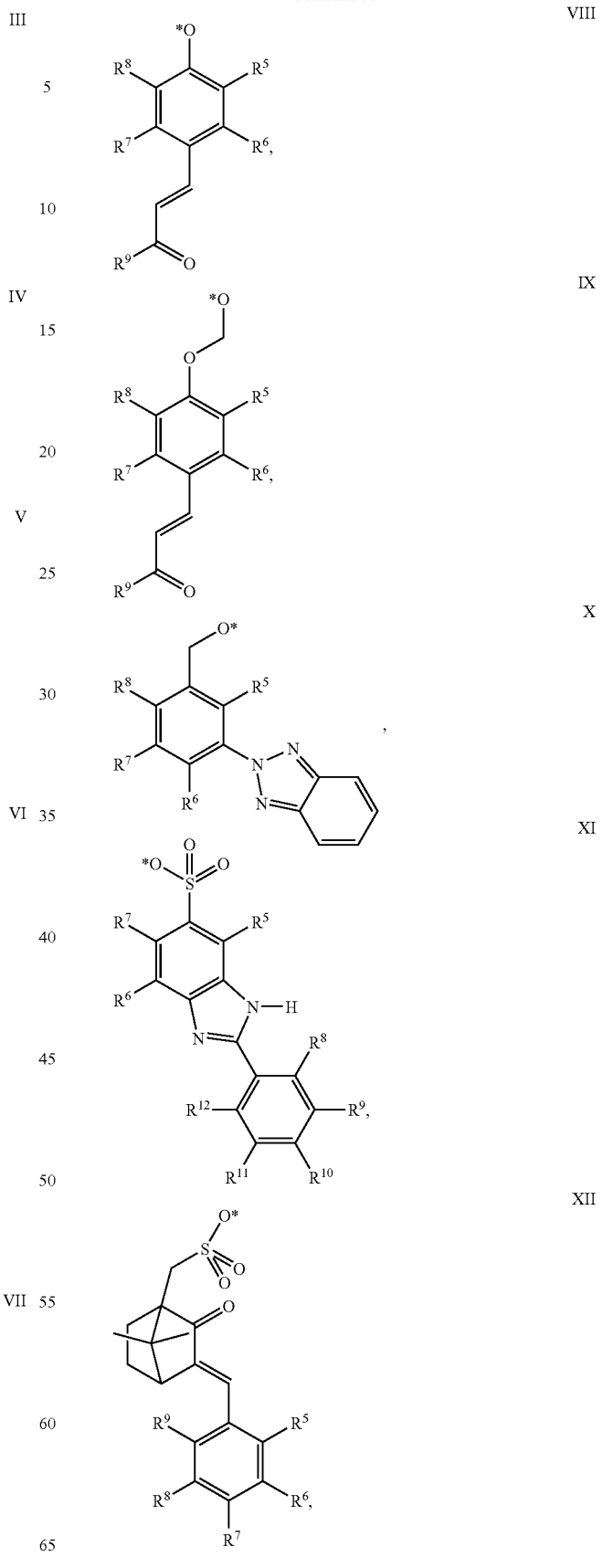

where

R$^5$ to R$^{16}$ each, independently of one another, denote H, —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl and A is alkyl having 1 to 4 C atoms, n is an integer from 1 to 25, X is the counterion to the cations [NHA$_2$]$^+$ and [NA$_3$]$^+$ or to the anion [SO$_3$]$^-$ and Y and Z are each, independently of one another, -ascorbyl, hydroxyl, —O-2-ethylhexyl, —O-hexyl, —OA or —NH—C(CH$_3$)$_3$, where for R$^5$ to R$^9$ in formula IV, the radicals H, OH and OA are excluded, apart from the case where at least one substituent from R$^5$ to R$^9$ denotes A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl and with the proviso that at least one of the radicals R$^3$ or R$^4$ stands for a radical B.

Advantages of the compounds or compositions according to the invention here besides the absorbent action as UV filters, as confirmed by way of example in FIG. 1 for DHAB (ascorbyl 2-(4-diethylamino-2-hydroxybenzoyl)benzoate), synthesised according to Example 1, are, in particular, the antioxidant action, which develops on functionalisation of the matrix through decomposition of the ascorbic acid skeleton, if appropriate the self-tanning action, which arises from the Maillard reaction, and in particular the functionalisation of the matrix, which, depending on the active-compound radical B in the compounds of the formula I, corresponds to immobilisation of the active compound and thus, for example, an immobilised UV-protection action or corresponds to a controlled release of active compound, for example a pharmacological active compound. However, the compounds according to the invention also have an anti-oxidant action for structural reasons.

For the purposes of the present invention, the term composition or formulation is used synonymously.

The agents here are usually either compositions which can be applied topically, for example cosmetic, pharmaceutical or dermatological formulations. In this case, the compositions comprise a cosmetically, pharmaceutically or dermatologically suitable vehicle and, depending on the desired property profile, optionally further suitable ingredients. The topical compositions are preferably employed as cosmetic or dermatological composition, particularly preferably as cosmetic composition.

The compounds of the formula I are typically employed in accordance with the invention in amounts of 0.01 to 20% by weight, preferably in amounts of 0.05% by weight to 10% by weight. The person skilled in the art is presented with absolutely no difficulties here in selecting the amounts correspondingly depending on the intended action of the composition.

The functionalisation of the matrix or the evidence of bonding can be checked with reference to some bonding tests. These bonding tests are described in the example part.

The agents according to the invention preferably comprise as little oxygen as possible, i.e. the agents should be prepared under inert-gas conditions.

It is furthermore advantageous to keep the water content low. It is furthermore advantageous to limit the presence of (heavy) metal ions since these, as is known, can destabilise antioxidants. Thus, the agents according to the invention may comprise, for example, complexing agents. During preparation and also storage, the substances according to the invention, and the agents comprising the substances according to the invention, should be protected against UV radiation, light and heat. If the agents comprise water, the pH should preferably be set in the acidic range. All measures in this respect are known to the person skilled in the art.

However, the protective action against oxidative stress or against the action of free radicals can be improved further if the agents or compositions according to the invention comprise one or more further antioxidants, where the person skilled in the art is presented with absolutely no difficulties in selecting antioxidants which act suitably quickly or in a time-delayed manner.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homo-cysteine sulfoximine, buthionine sulfones, penta-, hexa- and heptathionine sulfoximine) in very low tolerated doses (for example pmol to μmol/kg), and also (metal) chelating agents, (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosyl rutin, ferulic acid, furfurylidene-glucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, ZnSO$_4$), selenium and derivatives thereof (for example selenomethionine), stilbenes and derivatives thereof (for example stilbene oxide, trans-stilbene oxide).

Suitable antioxidants are also compounds of the general formula A or B

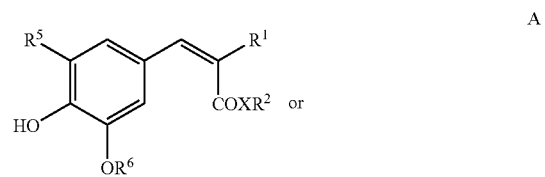

A

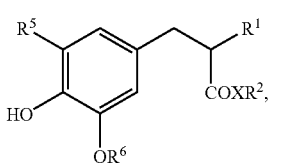

in which
R¹ can be selected from the group —C(O)CH₃, —CO₂R³, —C(O)NH₂ and —C(O)N(R⁴)₂,
X denotes O or NH,
R² denotes linear or branched alkyl having 1 to 30 C atoms,
R³ denotes linear or branched alkyl having 1 to 20 C atoms,
R⁴ in each case, independently of one another, denotes H or linear or branched alkyl having 1 to 8 C atoms,
R⁵ denotes linear or branched alkyl having 1 to 8 C atoms or linear or branched alkoxy having 1 to 8 C atoms and
R⁶ denotes linear or branched alkyl having 1 to 8 C atoms, preferably derivatives of 2-(4-hydroxy-3,5-dimethoxybenzylidene)malonic acid and/or 2-(4-hydroxy-3,5-dimethoxybenzyl)malonic acid, particularly preferably bis (2-ethylhexyl) 2-(4-hydroxy-3,5-dimethoxybenzylidene) malonate (for example Oxynex® ST liquid) and/or bis(2-ethylhexyl) 2-(4-hydroxy-3,5-dimethoxy-benzyl) malonate (for example RonaCare® AP).

Mixtures of antioxidants are likewise suitable for use in the agents or compositions according to the invention. Known and commercial mixtures are, for example, mixtures comprising, as active compounds, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed in such compositions with compounds of the formula I in ratios in the range from 1000:1 to 1:1000, preferably in amounts of 100:1 to 1:100.

The agents or compositions according to the invention may comprise vitamins as further ingredients. The cosmetic compositions according to the invention preferably comprise vitamins and vitamin derivatives selected from vitamin A, vitamin A propionate, vitamin A palmitate, vitamin A acetate, retinol, vitamin B, thiamine chloride hydrochloride (vitamin B₁), riboflavin (vitamin B₂), nicotinamide, vitamin C (ascorbic acid), vitamin D, ergocalciferol (vitamin D₂), vitamin E, DL-α-tocopherol, tocopherol E acetate, tocopherol hydrogensuccinate, vitamin K₁, esculin (vitamin P active compound), thiamine (vitamin B₁), nicotinic acid (niacin), pyridoxine, pyridoxal, pyridoxamine (vitamin B₆), pantothenic acid, biotin, folic acid and cobalamine (vitamin B₁₂), particularly preferably retinol, nicotinamide, vitamin A palmitate, vitamin C and derivatives thereof, DL-α-tocopherol, tocopherol E acetate, nicotinic acid, pantothenic acid and biotin, very particularly preferably retinol or nicotinamide. Vitamins are usually employed here with compounds of the formula I in ratios in the range from 1000:1 to 1:1000, preferably in amounts of 100:1 to 1:100.

Agents or compositions which are particularly preferred in accordance with the invention also comprise pure UV filters in addition to the compounds of the formula I.

In principle, all UV filters are suitable for combination with the compounds of the formula I according to the invention. Particular preference is given to UV filters whose physiological acceptability has already been demonstrated. Both for UVA and UVB filters, there are many proven substances known from the specialist literature, for example
benzylidenecamphor derivatives, such as 3-(4'-methylbenzylidene)-dl-camphor (for example Eusolex® 6300), 3-benzylidenecamphor (for example Mexoryl® SD), polymers of N-{(2 and 4)-[(2-oxoborn-3-ylidene)methyl]-benzyl}acrylamide (for example Mexoryl® SW), N,N,N-trimethyl-4-(2-oxoborn-3-ylidenemethyl)anilinium methylsulfate (for example Mexoryl®SK) or (2-oxoborn-3-ylidene)toluene-4-sulfonic acid (for example Mexoryl® SL),
benzoyl- or dibenzoylmethanes, such as 1-(4-tert-butylphenyl)-3-(4-methoxyphenyl)propane-1,3-dione (for example Eusolex® 9020) or 4-isopropyl-dibenzoylmethane (for example Eusolex® 8020),
benzophenones, such as 2-hydroxy-4-methoxybenzophenone (for example Eusolex® 4360) or 2-hydroxy-4-methoxybenzophenone-5-sulfonic acid and its sodium salt (for example Uvinul® MS-40),
methoxycinnamic acid esters, such as octyl methoxycinnamate (for example Eusolex® 2292), isopentyl 4-methoxycinnamate, for example as a mixture of the isomers (for example Neo Heliopan® E 1000),
salicylate derivatives, such as 2-ethylhexyl salicylate (for example Eusolex® OS), 4-isopropylbenzyl salicylate (for example Megasol®) or 3,3,5-trimethylcyclohexyl salicylate (for example Eusolex® HMS),
4-aminobenzoic acid and derivatives, such as 4-aminobenzoic acid, 2-ethylhexyl 4-(dimethylamino)benzoate (for example Eusolex® 6007), ethoxylated ethyl 4-aminobenzoate (for example Uvinul® P25),
phenylbenzimidazolesulfonic acids, such as 2-phenylbenzimidazole-5-sulfonic acid and potassium, sodium and triethanolamine salts thereof (for example Eusolex® 232), 2,2-(1,4-phenylene)bisbenzimidazole-4,6-disulfonic acid and salts thereof (for example Neoheliopan® AP) or 2,2-(1,4-phenylene)bisbenzimidazole-6-sulfonic acid;
and further substances, such as
2-ethylhexyl 2-cyano-3,3-diphenylacrylate (for example Eusolex® OCR),
3,3'-(1,4-phenylenedimethylene)bis(7,7-dimethyl-2-oxobicyclo[2.2.1]hept-1-ylmethanesulfonic acid and salts thereof (for example Mexoryl® SX) and
2,4,6-trianilino-(p-carbo-2'-ethylhexyl-1'-oxy)-1,3,5-triazine (for example Uvinul® T 150)
hexyl 2-(4-diethylamino-2-hydroxybenzoyl)benzoate (for example Uvinul®UVA Plus, BASF).

The compounds mentioned in the list should only be regarded as examples. It is of course also possible to use other UV filters.

These organic UV filters are generally incorporated into cosmetic formulations in an amount of 0.5 to 10 percent by weight, preferably 1-8% by weight.

Further suitable organic UV filters are, for example,
2-(2H-benzotriazol-2-yl)-4-methyl-6-(2-methyl-3-(1,3,3,3-tetramethyl-1-(trimethylsilyloxy)disiloxanyl)propyl) phenol (INCI: Drometrizole Trisiloxane, for example Mexoryl® XL),
α-(trimethylsilyl)-ω-[trimethylsilyl)oxy]poly[oxy(dimethyl [and approximately 6% of methyl[2-[p-[2,2-bis (ethoxycarbonyl)vinyl]phenoxy]-1-methyleneethyl]] and approximately 1.5% of methyl[3-[p-[2,2-bis (ethoxy-carbonyl)vinyl)phenoxy)propenyl) and 0.1 to 0.4% of (methylhydrogen]-silylene]] (n≈60) (CAS No. 207 574-74-1) (INCI: Polysilicone-15, for example Parsol® SLX), 2,2'-methylenebis(6-(2H-benzotriazol-2-yl)-4-(1,1,3,3-tetramethylbutyl)-phenol) (CAS No. 103 597-45-1) (INCI: Methylene Bis-Benzotriazolyl Tetramethylbutylphenol, for example Tinosorb® M), 2,2'-(1,4-phenylene)bis(1H-benzimidazole-4,6-disulfonic acid, mono-sodium salt) (CAS No. 180 898-37-7), 2,4-bis{[4-(2-ethylhexyloxy)-2-hydroxy]phenyl}-6-(4-methoxyphenyl)-1,3,5-triazine (CAS No. 103 597-45-, 187 393-00-6) (INCI: Bis-Ethyl-hexyloxyphenol Methoxyphenyl Triazine, for example Tinosorb®S) or 2-ethylhexyl 4,4'-[(6-[4-((1,1-dimethylethyl)aminocarbonyl)phenylamino]-1,3,5-triazine-2,4-diyl)diimino]bis (benzoate) (INCI: Diethylhexyl Butamido Triazone, for example Uvasorb® HEB).

Organic UV filters are generally incorporated into cosmetic formulations in an amount of 0.5 to 20 percent by weight, preferably 1-15% by weight.

Conceivable inorganic UV filters are those from the group of the titanium dioxides, such as, for example, coated titanium dioxide (for example Eusolex®T-2000, Eusolex®T-AQUA, Eusolex®T-AVO), zinc oxides (for example Sachtotec®), iron oxides or also cerium oxides. These inorganic UV filters are generally incorporated into cosmetic compositions in an amount of 0.5 to 20 per cent by weight, preferably 2-10%.

Combination of one or more compounds of the formula I with further UV filters enables the protective action against damaging effects of UV radiation to be optimised. Broadband protection systems thereby arise, which can also be supplemented by addition of inorganic UV filters.

All the said UV filters can also be employed in encapsulated form. In particular, it is advantageous to employ organic UV filters in encapsulated form. In detail, the following advantages arise:

The hydrophilicity of the capsule wall can be set independently of the solubility of the UV filter. Thus, for example, it is also possible to incorporate hydrophobic UV filters into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in cosmetic compositions. Encapsulation of these filters or compounds which impair the photostability of these filters, such as, for example, cinnamic acid derivatives, enables the photostability of the entire composition to be increased.

Skin penetration by organic UV filters and the associated potential for irritation on direct application to the human skin is repeatedly being discussed in the literature. The encapsulation of the corresponding substances which is proposed here suppresses this effect.

In general, encapsulation of individual UV filters or other ingredients enables composition problems caused by the interaction of individual composition constituents with one another, such as crystallisation processes, precipitation and agglomerate formation, to be avoided since the interaction is suppressed.

It is therefore preferred in accordance with the invention for one or more of the above-mentioned UV filters to be in encapsulated form. It is advantageous here for the capsules to be so small that they cannot be viewed with the naked eye. In order to achieve the above-mentioned effects, it is further more necessary for the capsules to be sufficiently stable and the encapsulated active compound (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules particularly preferably to be employed in accordance with the invention have walls which can be obtained by a sol-gel process, as described in the applications WO 00/09652, WO 00/72806 and WO 00/71084. Preference is again given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules are preferably present in agents or compositions according to the invention in amounts which ensure that the encapsulated UV filters are present in the composition in the above-indicated amounts.

The agents or compositions according to the invention may in addition comprise further antiageing active compounds, anticellulite active compounds or conventional skin-protecting or skin-care active compounds. Skin-protecting or skin-care active compounds can in principle be any active compounds known to the person skilled in the art.

Particularly preferred antiageing active compounds are pyrimidinecarboxylic acids, aryl oximes, bioflavonoids, bioflavonoid-containing extracts, chromones or retinoids.

Pyrimidinecarboxylic acids occur in halophilic microorganisms and play a role in osmoregulation of these organisms (E. A. Galinski et al., Eur. J. Biochem., 149 (1985) pages 135-139). Of the pyrimidinecarboxylic acids, particular mention should be made here of ectoine ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid and derivatives thereof. These compounds stabilise enzymes and other biomolecules in aqueous solutions and organic solvents. They furthermore stabilise, in particular, enzymes against denaturing conditions, such as salts, extreme pH values, surfactants, urea, guanidinium chloride and other compounds.

Ectoine and ectoine derivatives, such as hydroxyectoine, can advantageously be used in medicaments. In particular, hydroxyectoine can be employed for the preparation of a medicament for the treatment of skin diseases. Other areas of application of hydroxyectoine and other ectoine derivatives are typically in areas in which, for example, trehalose is used as additive. Thus, ectoine derivatives, such as hydroxyectoine, can be used as protectant in dried yeast and bacteria cells. Pharmaceutical products, such as non-glycosylated, pharmaceutical active peptides and proteins, for example t-PA, can also be protected with ectoine or its derivatives.

Of the cosmetic applications, particular mention should be made of the use of ectoine and ectoine derivatives for the care of aged, dry or irritated skin. Thus, European patent application EP-A-0 671 161 describes, in particular, that ectoine and hydroxyectoine are employed in cosmetic compositions, such as powders, soaps, surfactant-containing cleansing products, lipsticks, rouge, make-up, care creams and sunscreen preparations.

Preference is given here to the use of a pyrimidinecarboxylic acid of the following formula

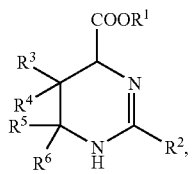

in which $R^1$ is a radical H or $C_{1-8}$-alkyl, $R^2$ is a radical H or $C_{1-4}$-alkyl, and $R^3$, $R^4$, $R^5$ and $R^6$ are each, independently of one another, a radical from the group H, OH, $NH_2$ and $C_{1-4}$-alkyl. Preference is given to the use of pyrimidinecarboxylic acids in which $R^2$ is a methyl or ethyl group and $R^1$ or $R^5$ and $R^6$ are H. Particular preference is given to the use of the pyrimidine-carboxylic acids ectoine ((S)-1,4,5,6-tetrahydro-2-methyl-4-pyrimidine-carboxylic acid) and hydroxyectoine ((S,S)-1,4,5,6-tetrahydro-5-hydroxy-2-methyl-4-pyrimidinecarboxylic acid). The compositions according to the invention preferably comprise pyrimidinecarboxylic acids of this type in amounts of up to 15% by weight. The pyrimidinecarboxylic acids are preferably employed here in ratios of 100:1 to 1:100 with respect to the compounds of the formula I, with ratios in the range 1:10 to 10:1 being particularly preferred.

Of the aryl oximes, preference is given to the use of 2-hydroxy-5-methyl-laurophenone oxime, which is also known as HMLO, LPO or F5. Its suitability for use in cosmetic agents is disclosed, for example, in DE-A-41 16 123. Compositions which comprise 2-hydroxy-5-methyllauro-phenone oxime are accordingly suitable for the treatment of skin diseases which are associated with inflammation. The compositions here preferably comprise 0.01 to 10% by weight of the aryl oxime, it being particularly preferred for the composition to comprise 0.05 to 5% by weight of aryl oxime.

Known bioflavonoids are, for example, troxerutin, tiliroside, □-glucosylrutin, rutin or isoquercetin, where the said choice is not intended to have a restrictive effect.

Bioflavonoid-containing extracts are, for example, gingko biloba or emblica.

Known antiageing substances are also chromones, as described, for example, in EP 1508327, or retinoids, for example retinol (vitamin A), retinoic acid, retinaldehyde or also synthetically modified compounds of vitamin A.

The chromones and retinoids described are simultaneously also effective anti-cellulite active compounds. A likewise known anticellulite active compound is caffeine.

The agents may include or comprise, essentially consist of or consist of the said necessary or optional constituents or restrictions. All compounds or components which can be used in the agents or compositions are either known and commercially available or can be synthesised by known processes.

The one or more compounds of the formula I can be incorporated into cosmetic or dermatological compositions in a conventional manner. Suitable compositions are those for external use, for example in the form of a cream, lotion, gel or as a solution which can be sprayed onto the skin.

Examples which may be mentioned of application forms of the compositions according to the invention are: solutions, suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower compositions. Any desired customary vehicles, auxiliaries and, if desired, further active compounds may be added to the composition.

Preferred auxiliaries originate from the group of the preservatives, stabilisers, solubilisers, colorants, odour improvers.

Ointments, pastes, creams and gels may comprise the customary vehicles, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propyl-ene glycol, 1,3-butyl glycol, dimethyl capramide, dimethyl isosorbide, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

In a preferred application, the ascorbic acid derivatives according to the invention are, as described, converted into an application-suitable formulation just before use. For example, the substance is dissolved in a vehicle, as described above, and applied directly to skin or preferably to hair. Particularly suitable vehicles in this sense are Arlasolve DMI (Dimethylisosorbide), Butylene Glycol, Finsolv® PG-22 (Dipropylene Glycol Dibenzoate) or Pelemol® BIP (Butylphthalimide Isopropylphthalimide).

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, mascara, eyeliner, eye shadow, rouge, powder make-up, emulsion make-up and wax make-up, and sunscreen, pre-sun and after-sun preparations.

The preferred composition forms according to the invention include, in particular, emulsions.

Emulsions according to the invention are advantageous and comprise, for example, the said fats, oils, waxes and other lipids, as well as water and an emulsifier, as usually used for a composition of this type.

The lipid phase may advantageously be selected from the following group of substances:

mineral oils, mineral waxes;

oils, such as triglycerides of capric or caprylic acid, furthermore natural oils, such as, for example, castor oil;

fats, waxes and other natural and synthetic lipids, preferably esters of fatty acids with alcohols having a low carbon number, for example with isopropanol, propylene glycol or glycerol, or esters of fatty alcohols with alkanoic acids having a low carbon number or with fatty acids;

silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of the esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, from the group of the esters of aromatic carboxylic acids and saturated and/or unsaturated, branched and/or unbranched alcohols having a chain length of 3 to 30 C atoms. Ester oils of this type can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethyl-hexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group of the branched and unbranched hydrocarbons and hydrocarbon waxes, silicone oils, dialkyl ethers, the group of the saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18, C atoms. The fatty acid triglycerides may advantageously be selected, for example, from the group of the synthetic, semi-synthetic and natural oils, for example olive oil, sunflower oil, soya oil, peanut oil, rape-seed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The oil phase is advantageously selected from the group 2-ethylhexyl isostearate, octyldodecanol, isotridecyl isononanoate, isoeicosane, 2-ethyl-hexyl cocoate, $C_{12-15}$-alkyl benzoate, caprylic/capric acid triglyceride, dicapryl ether.

Particularly advantageous are mixtures of $C_{12-15}$-alkyl benzoate and 2-ethyl-hexyl isostearate, mixtures of $C_{12-15}$-alkyl benzoate and isotridecyl isononanoate, as well as mixtures of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil to be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane, poly(methylphenylsiloxane).

Also particularly advantageous are mixtures of cyclomethicone and iso-tridecyl isononanoate, of cyclomethicone and 2-ethylhexyl isostearate.

The aqueous phase of the compositions according to the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984, 5984, in each case individually or in combination.

In particular, mixtures of the above-mentioned solvents are used. In the case of alcoholic solvents, water may be a further constituent.

Emulsions according to the invention are advantageous and comprise, for example, the said fats, oils, waxes and other lipids, as well as water and an emulsifier, as usually used for a formulation of this type.

In a preferred embodiment, the compositions according to the invention comprise hydrophilic surfactants.

The hydrophilic surfactants are preferably selected from the group of the alkylglucosides, acyl lactylates, betaines and coconut amphoacetates.

The alkylglucosides are themselves advantageously selected from the group of the alkylglucosides which are distinguished by the structural formula

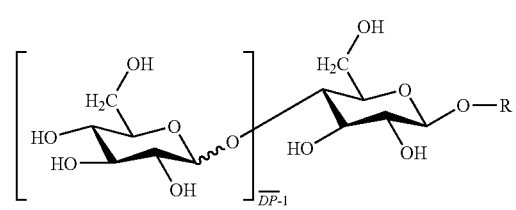

where R represents a branched or unbranched alkyl radical having 4 to 24 carbon atoms, and where $\overline{DP}$ denotes a mean degree of glucosylation of up to 2.

The value $\overline{DP}$ represents the degree of glucosidation of the alkylglucosides used in accordance with the invention and is defined as $$\overline{DP} = \frac{p_1}{100} \cdot 1 + \frac{p_2}{100} \cdot 2 + \frac{p_3}{100} \cdot 3 + \ldots = \sum \frac{p_i}{100} \cdot i$$

in which $p_1, p_2, p_3 \ldots p_i$ represent the proportion of mono-, di-, tri- ... i-fold glucosylated products in percent by weight. Advantageous in accordance with the invention is the selection of products having degrees of glucosylation of 1-2, particularly advantageously of 1.1 to 1.5, very particularly advantageously of 1.2-1.4, in particular of 1.3.

The value DP takes into account the fact that alkylglucosides generally, as a consequence of their preparation, represent mixtures of mono- and oligo-glucosides. A relatively high content of monoglucosides, typically in the order of 40-70% by weight, is advantageous in accordance with the invention.

Alkylglycosides which are particularly advantageously used in accordance with the invention are selected from the group octyl glucopyranoside, nonyl glucopyranoside, decyl glucopyranoside, undecyl glucopyranoside, dodecyl glucopyranoside, tetradecyl glucopyranoside and hexadecyl gluco-pyranoside.

It is likewise advantageous to employ natural or synthetic raw materials and auxiliaries or mixtures which are distinguished by an effective content of the active compounds used in accordance with the invention, for example Plantaren® 1200 (Henkel KGaA), Oramix® NS 10 (Seppic).

The acyllactylates are themselves advantageously selected from the group of the substances which are distinguished by the structural formula

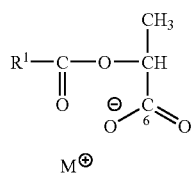

where $R^1$ denotes a branched or unbranched alkyl radical having 1 to 30 carbon atoms and $M^+$ is selected from the group of the alkali metal ions and the group of ammonium ions which are substituted by one or more alkyl and/or one or more hydroxyalkyl radicals, or corresponds to half an equivalent of an alkaline-earth metal ion.

For example, sodium isostearyl lactylate, for example the product Pathionic® ISL from the American Ingredients Company, is advantageous.

The betaines are advantageously selected from the group of the substances which are distinguished by the structural formula

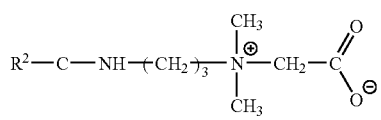

where $R^2$ denotes a branched or unbranched alkyl radical having 1 to 30 carbon atoms.

$R^2$ particularly advantageously denotes a branched or unbranched alkyl radical having 6 to 12 carbon atoms.

For example, capramidopropylbetaine, for example the product Tego® Betain 810 from Th. Goldschmidt AG, is advantageous.

A coconut amphoacetate which is advantageous in accordance with the invention is, for example, sodium coconut amphoacetate, as available under the name Miranol® Ultra C32 from Miranol Chemical Corp.

The compositions according to the invention are advantageously characterised in that the hydrophilic surfactant(s) is (are) present in concentrations of 0.01-20% by weight, preferably 0.05-10% by weight, particularly preferably 0.1-5% by weight, in each case based on the total weight of the composition.

For use, the cosmetic and dermatological compositions according to the invention are applied to the skin and/or the hair in an adequate amount in the usual manner for cosmetics.

Cosmetic and dermatological compositions according to the invention can exist in various forms. Thus, they can be, for example, a solution, a water-free composition, an emulsion or microemulsion of the water-in-oil (W/O) type or of the oil-in-water (O/W) type, a multiple emulsion, for example of the water-in-oil-in-water (W/O/W) type, a gel, a solid stick, an ointment or an aerosol. It is also advantageous to administer ectoine in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions according to the invention.

Co-emulsifiers which are advantageous in accordance with the invention are, for example, O/W emulsifiers, principally from the group of the substances having HLB values of 11-16, very particularly advantageously having HLB values of 14.5-15.5, so long as the O/W emulsifiers have saturated radicals R and R'. If the O/W emulsifiers have unsaturated radicals R and/or R' or in the case of isoalkyl derivatives, the preferred HLB value of such emulsifiers may also be lower or higher.

It is advantageous to select the fatty alcohol ethoxylates from the group of the ethoxylated stearyl alcohols, cetyl alcohols, cetylstearyl alcohols (cetearyl alcohols). Particular preference is given to the following: polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group:

polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate, An ethoxylated alkyl ether carboxylic acid or salt thereof which can advantageously be used is sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

Optional W/O emulsifiers, but ones which may nevertheless be advantageously employed in accordance with the invention are the following:

fatty alcohols having 8 to 30 carbon atoms, monoglycerol esters of saturated and/or unsaturated, branched and/or unbranched alkanecarboxylic acids having a chain length of 8 to 24, in particular 12-18, C atoms, diglycerol esters of saturated and/or unsaturated, branched and/or unbranched alkanecarboxylic acids having a chain length of 8 to 24, in particular 12-18, C atoms, monoglycerol ethers of saturated and/or unsaturated, branched and/or unbranched alcohols having a chain length of 8 to 24, in particular 12-18, C atoms, diglycerol ethers of saturated and/or unsaturated, branched and/or unbranched alcohols having a chain length of 8 to 24, in particular 12-18, C atoms, propylene glycol esters of saturated and/or unsaturated, branched and/or unbranched alkanecarboxylic acids having a chain length of 8 to 24, in particular 12-18, C atoms, and sorbitan esters of saturated and/or unsaturated, branched and/or unbranched alkanecarboxylic acids having a chain length of 8 to 24, in particular 12-18, C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate or PEG 30 dipolyhydroxystearate.

The agents or compositions described are particularly suitable for protecting human skin against UV radiation, ageing processes and against oxidative stress, i.e. against damage caused by free radicals. In this connection, they are in the various administration forms usually used for this application. For example, the composition may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The composition may comprise cosmetic adjuvants which are usually used in this type of composition, such as, for example, thickeners, softeners, moisturisers, surface-active agents, emulsifiers, preservatives, antifoams, perfumes, waxes, lanolin, propellants, dyes and/or pigments which colour the composition itself or the skin, and other ingredients usually used in cosmetics.

The dyes used are preferably approved dyes which are listed in the Cosmetics Regulation, Annex 3, as positive list.

The preservatives used are preferably approved preservatives which are listed in the Cosmetics Regulation, Annex 6, as positive list or also anti-microbial pigments, as described, for example, in WO 2004/0092283 or WO 2004/091567.

Suitable preservatives are therefore also alkyl esters of p-hydroxybenzoic acid, hydantoin derivatives, propionate salts or a multiplicity of ammonium compounds.

Very particularly preferred preservatives are methylparaben, propylparaben, imidazolidinylurea, sodium dehydroxyacetate or benzyl alcohol. Preservatives are employed in amounts between 0.5 and 2% by weight.

Emollients or softeners are often incorporated into cosmetic compositions. They are preferably employed in 0.5 to 50% by weight, preferably between 5 and 30% by weight, based on the composition as a whole. In general, softeners can be classified in classes, such as, for example, the category of the esters, fatty acids or fatty alcohols, polyols, hydrocarbons and oils containing at least one amide structural unit.

Representative oils containing at least one amide structural unit together with their synthesis are described, in particular, in EP 1044676 and EP 0928608. A compound which is particularly preferred indicated is isopropyl N-lauroylsarcosinate, which is commercially available from Ajinomoto under the product name Eldew SL-205.

Of the esters, mono- or diesters can be selected. Examples in this respect are dibutyl adipate, diethyl sebacate, diisopropyl dimerate or dioctyl succinate. Branched fatty acid esters are, for example, 2-ethylhexyl myristate, isopropyl stearate or isostearyl palmitate. Tribasic esters are, for example, triisopropyl trilinoleate or trilauryl citrate. Straight-chain fatty acid esters are, for example, lauryl palmitate, myristyl lactate, oleyl erucate or stearyl oleate. Preferred esters are Coco-Caprylate/Caprate (=INCI name, these are esters made from coconut fatty alcohols with saturated medium-chain fatty acids), propylene glycol myristyl ether acetate, diisopropyl adipate or cetyl octanoate.

Suitable fatty alcohols and acids are compounds which have 10 to 20 C atoms. Particularly preferred compounds are cetyl, myristyl, palmitic or stearic alcohol or acid.

Suitable polyols are linear or branched-chain alkylpolyhydroxyl compounds, for example propylene glycol, sorbitol or glycerol. However, it is also possible to employ polymeric polyols, for example polypropylene glycol or polyethylene glycol. Butylene glycol and propylene glycol are also particularly suitable compounds for enhancing the penetration capacity.

Examples of hydrocarbons as softeners are compounds which generally have 12 to 30 C atoms. Specific examples are arylalkyl benzoates, alkyl benzoates, mineral oils, Vaseline, squalenes or isoparaffins.

Further emollients or hydrophobicising agents are preferably $C_{12}$ to $C_{15}$ alkyl benzoates, dioctyl adipate, octyl stearate, octyldodecanol, hexyl laurate, octyldodecyl neopentanoate, cyclomethicone, dicaprylic ether, dimethicone, phenyltrimethicone, isopropyl myristate, caprylic/capric glyceride, propylene glycol dicaprylate/dicaprate or decyl oleate.

A further category of functional ingredients of cosmetic compositions in the sense of the invention are thickeners. Thickeners are generally employed in amounts between 0.1 to 20% by weight, preferably between 0.5 to 10% by weight, based on the total amount. Examples of these compounds are crosslinked polyacrylate materials, commercially available from B. F. Goodrich Company under the trade name Carbopol. It is also possible to use thickeners such as xanthan gum, carrageenan gum, gelatine gum, karaya gum, pectin gum or carob seed flour.

Under certain circumstances, it is possible for a compound to be both a thickener and also a softener. Examples thereof are silicone gums (kinematic viscosity >10 centistokes), esters, such as, for example, glycerol stearate, or cellulose derivatives, for example hydroxypropylcellulose.

The dispersant or solubiliser used can be an oil, wax or other lipid, a lower monoalcohol or lower polyol or mixtures thereof. Particularly preferred monoalcohols or polyols include ethanol, i-propanol, propylene glycol, glycerol and sorbitol.

A preferred embodiment of the invention is an emulsion in the form of a protective cream or milk which, in addition to the compound(s) of the formula I, comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The composition according to the invention or the agent may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other lipids.

If a composition is formulated as an aerosol, the customary propellants, such as alkanes, fluoroalkanes and chlorofluoroalkanes, are generally used.

The cosmetic composition may also be used to protect the hair against photochemical damage in order to prevent colour changes, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling and treating the hair, in the form of a lotion or gel for brushing or blow-waving, in the form of a hair lacquer, permanent waving composition, colorant or bleach for the hair. Besides the compound(s) of the formula I, the composition having light-protection properties may comprise various adjuvants used in this type of composition, such as surface-active agents, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

The present invention furthermore relates to a process for the preparation of an agent, as described above, characterised in that at least one compound of the formula I is mixed with a vehicle and optionally with further active compounds or auxiliaries. The present invention also relates to a process for the preparation of a composition which is characterised in that at least one compound of the formula I containing radicals as described above is mixed with a cosmetically, pharmaceutically or dermatologically suitable vehicle.

The compositions or agents according to the invention can be prepared here with the aid of techniques which are well known to the person skilled in the art.

The mixing can result in dissolution, emulsification or dispersion of the compound of the formula I in the vehicle.

The invention is explained in greater detail below with reference to examples. The invention can be carried out throughout the range claimed and is not restricted to the examples given here.

EXAMPLES

List of Abbreviations Used
eq. equivalent
DCC dicyclohexylcarbodiimide
DMAP dimethylaminopyridine
DMSO dimethyl sulfoxide
EDC N-(3-dimethylaminopropyl)-N'-ethylcarbodiimide hydrochloride
EA ethyl acetate
EG ethylene glycol
sat. saturated
conc. concentrated
1 N HCl 1 N hydrochloric acid
i-PrOH isopropanol
soln. solution
MeCN acetonitrile
MTBE methyl tert-butyl ether
org. organic
RT room temperature
hr. hour
T temperature
THF tetrahydrofuran

Example 1

Synthesis of (R)-2-((R)-3,4-dihydroxy-5-oxo-2,5-dihydrofuran-2-yl)-2-hydroxyethyl 2-(4-diethylamino-2-hydroxybenzoyl)benzoate (or synonymously ascorbyl 2-(4-diethylamino-2-hydroxybenzoyl)benzoate)

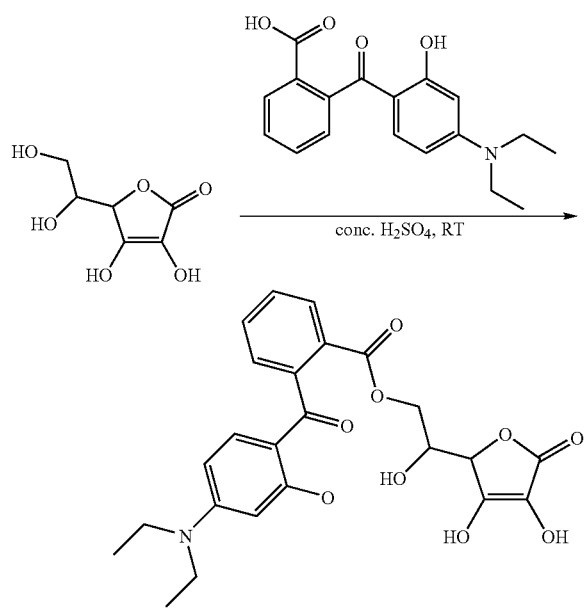

Vitamin C (14.1 g; 79.78 mmol, 5 eq.) is introduced in portions into 70 ml of conc. sulfuric acid in an argon-flushed apparatus. The internal temperature is kept below 5° C. during this operation by ice-cooling. 5 g of 2-(4-diethyl-amino-2-hydroxybenzoyl)benzoic acid (16 mmol, 1 eq.) are subsequently introduced in portions, likewise at T<5° C. After a reaction time of 96 hrs. (thawing to room temperature), the reaction solution is poured into 350 ml of ice-water. 140 ml of 32% NaOH soln. are added dropwise with cooling. A violet oil forms, which separates from the aqueous solution (soln.). The aqueous soln. is poured off and extracted 3 times with ethyl acetate. After drying over sodium sulfate, the solvent is removed in vacuo, giving the product as a yellow foam (5.5 g; 73.8%).

Melting range: 90-120° C.

In this reaction procedure, the compound (R)-1-((R)-3,4-dihydroxy-5-oxo-2,5-dihydrofuran-2-yl)-2-hydroxyethyl 2-(4-diethylamino-2-hydroxybenzoyl)-benzoate also forms as a consequence of the synthesis. The proportion of this compound in the mixture is between 0 and 25%.

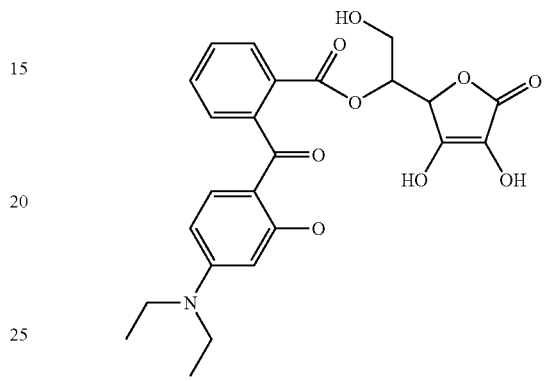

(R)-1-((R)-3,4-dihydroxy-5-oxo-2,5-dihydrofuran-2-yl)-2-hydroxyethyl 2-(4-diethylamino-2-hydroxybenzoyl)benzoate A UV spectrum of the product from Example 1 is shown in FIG. 1.

Depending on the pH, these compounds can carry partial charges, as shown below for the compound (R)-2-((R)-3,4-dihydroxy-5-oxo-2,5-dihydro-furan-2-yl)-2-hydroxyethyl 2-(4-diethylamino-2-hydroxybenzoyl)benzoate:

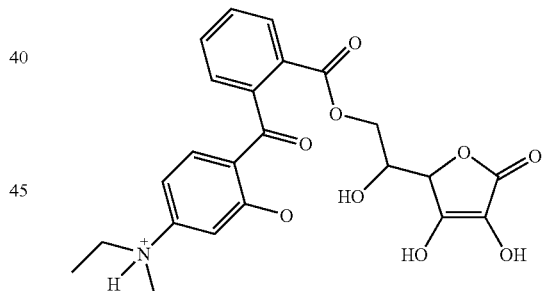

as ammonium compound,

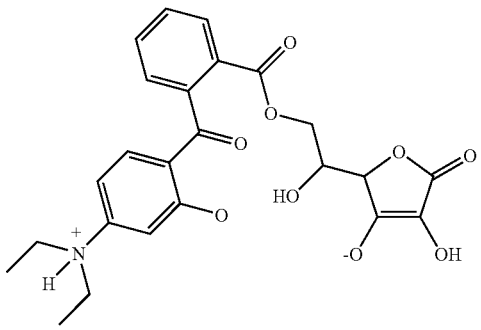

as zwitterionic compound or

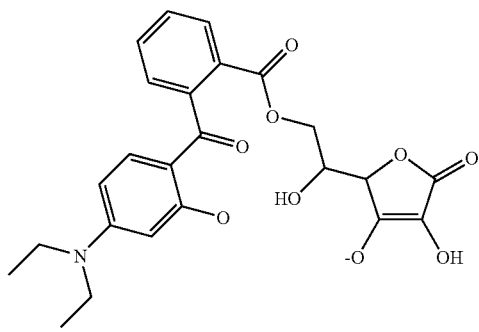

as ascorbate.

NMR data of (R)-2-((R)-3,4-dihydroxy-5-oxo-2,5-dihydrofuran-2-yl)-2-hydroxyethyl 2-(4-diethylamino-2-hydroxybenzoyl)benzoate 1H-NMR ($D_6$-DMSO): 1.10 (t, 6H), 3.39 (q, 4H), 3.98 (m, 1H), 4.13 (dd, 1H), 4.20 (dd, 1H) 4.57 (d, 1H), 5.35 (d, 1H), 6.07 (d, 1H), 6.18 (dd, 1H), 6.81 (d, 1H), 7.43 (dd, 1H), 7.65 (dt, 1H), 7.74 (dt; 1H), 8.08, (dd, 1H), 8.33 (br, 1H), 11.03 (br, 1H), 12.47 (s, 1H) ppm.

$^{13}$C-NMR ($D_6$-DMSO): 12.4, 20.7, 44.1, 65.3, 74.9, 96.4, 104.1, 109.0, 118.1, 127.9, 128.1, 129.5, 130.2, 132.6, 134.2, 140.2, 152.1, 153.7, 164.8, 165.0, 169.9, 197.5 ppm.

Example 2

Alternative Synthesis of 2-(3,4-dihydroxy-5-oxo-2,5-dihydrofuran-2-yl)-2-hydroxyethyl 2-(4-diethylamino-2-hydroxybenzoyl)benzoate

A)

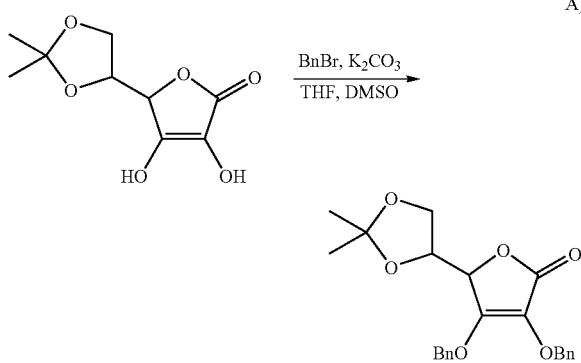

10 g of 5,6-isopropylidene ascorbate (46.3 mmol, 1 eq., available from Merck-Schuchardt: 8.18234) are dissolved in 30 ml of THF and 35 ml of DMSO, 19.2 g of potassium carbonate are added, and 13 ml of benzyl bromide (110 mmol, 2.4 eq.) are added dropwise. After 3 hrs. at 50° C., the evolution of gas is complete. The solid is filtered off and extracted 3 times with 100 ml of ethyl acetate each time. The combined organic phases are dried over sodium sulfate, and the solvent is removed in vacuo, giving the product virtually quantitatively without further purification.

B)

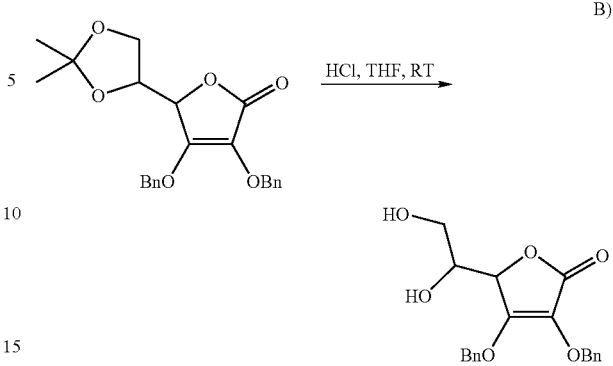

The di-benzyl-protected 5,6-isopropylidene ascorbate is dissolved in 65 ml of THF, and 30 ml of 2 N HCl are slowly added at room temperature. After 48 hrs., 150 ml of MTBE and solid sodium chloride are added to saturation, and the mixture is extracted. The organic phase is dried over sodium sulfate, and the solvent is removed in vacuo, giving the product virtually quantitatively without further purification.

C)

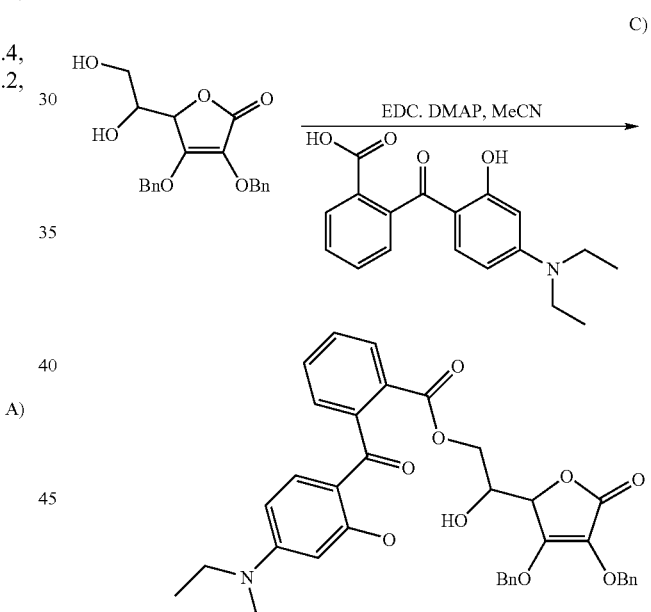

The di-benzyl-protected ascorbate (2.14 g; 6 mmol, 1 eq.) from step B) is dissolved in 11 ml of acetonitrile with DMAP (73 mg, 0.6 mmol, 0.1 eq.) and 1.88 g of 2-(4-diethylamino-2-hydroxybenzoyl)benzoic acid (6 mmol, 1 eq.) in an argon-flushed flask. The EDC (1.7 g; 9 mmol, 1.5 eq.) is then added in portions at 0° C. The mixture is warmed to RT, and the solvent is removed in vacuo after 22 hrs. The residue is taken up with 50 ml of ethyl acetate and 50 ml of 1 N NaOH soln. and extracted. The org. phase is subsequently extracted with 2×50 ml of 1 N HCl and 1×50 ml of sat. NaCl soln. The organic phase is dried over sodium sulfate, and the solvent is removed in vacuo, giving the product after filtration through silica gel.

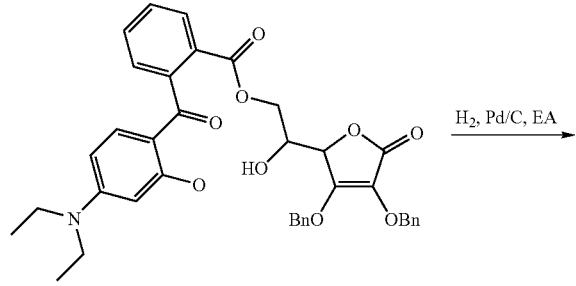

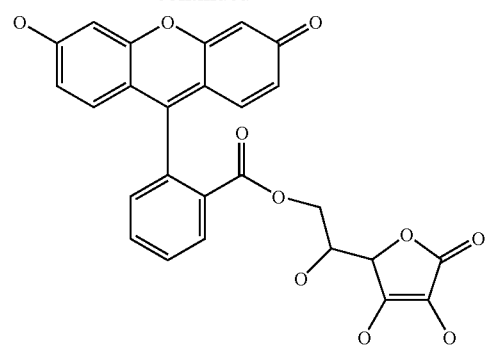

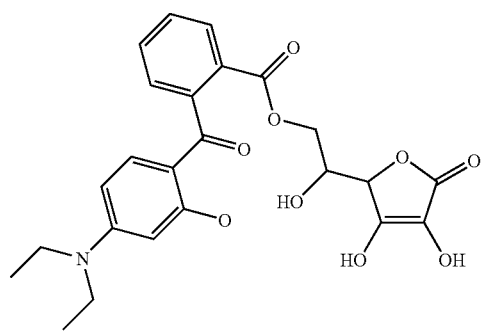

The starting material from step C) is dissolved in ethyl acetate and reduced using Pd/C catalyst under a hydrogen pressure of 1-5 bar. After filtration of the catalyst, the product is purified by filtration through silica gel.

Example 3

Synthesis of fluorescein 6-O-ascorbate (2-(3,4-dihydroxy-5-oxo-2,5-di-hydrofuran-2-yl)-2-hydroxyethyl 2-(6-hydroxy-3-oxo-3H-xanthen-9-yl)-benzoate)

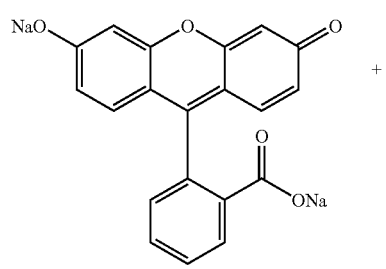

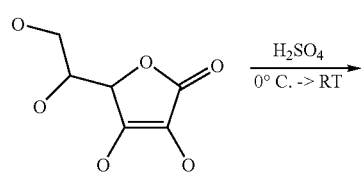

50 ml of conc. sulfuric acid are initially introduced in an argon-flushed 3-necked flask and cooled to 0° C. 14.05 g (79.8 mmol, 5 eq.) of ascorbic acid and subsequently 6.05 g of fluorescein-sodium (15.96 mmol, 1 eq.) are added in portions. After a reaction time of 16 hrs. at room temperature, the reaction solution is poured onto 250 g of ice, saturated with 80 g of sodium chloride and extracted 3× with 150 ml of ethyl methyl ketone. The combined org. phases are extracted with 100 ml of sat. NaCl solution, dried over sodium sulfate, and the solvent is removed in vacuo. Crystallisation from ethyl acetate gives the product as a red solid.

Example 4

Synthesis of sorbic acid 6-O-ascorbate [2-(3,4-dihydroxy-5-oxo-2,5-dihydro-furan-2-yl)-2-hydroxyethyl (2E,4E)-hexa-2,4-dienoate]

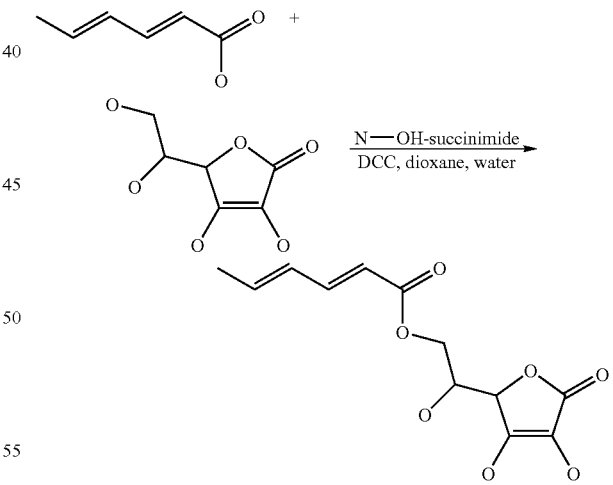

5 g of sorbic acid are dissolved in 50 ml of dioxane in a 3-necked flask, and 5.6 g of N-hydroxysuccinimide (49 mmol, 1.1 eq.) and 10.1 g of DCC (49 mmol, 1.1 eq.) are added successively. After a reaction time of 16 hrs. at room temperature, 39.3 g (223 mmol, 5 eq.) of ascorbic acid dissolved in 50 ml of water are added, and the mixture is stirred at room temperature for 16 h. The solvent is removed in vacuo, the residue is partitioned between 100 ml of dichloromethane and 100 ml of water and extracted. After drying over sodium sulfate, the solvent is removed in vacuo. Crystallisation from ethyl acetate gives the product as a white solid.

Example 5

Synthesis of indomethacin 6-O-ascorbate {2-(3,4-dihydroxy-5-oxo-2,5-di-hydrofuran-2-yl)-2-hydroxyethyl [1-(4-chlorobenzoyl)-5-methoxy-2-methyl-1H-indol-3-yl]acetate}

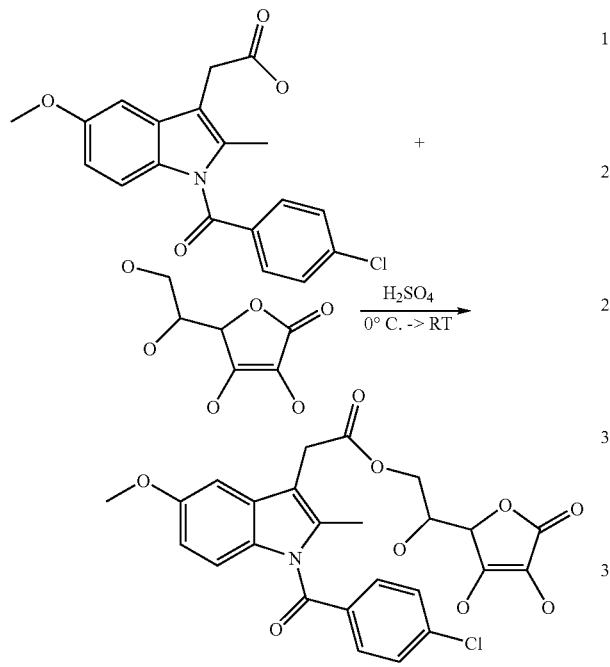

50 ml of conc. sulfuric acid are initially introduced in an argon-flushed 3-necked flask and cooled to 0° C. 14.05 g (79.8 mmol, 5 eq.) of ascorbic acid and subsequently 5.71 g of indomethacin (15.96 mmol, 1 eq.) are added in portions. After a reaction time of 16 hrs. at room temperature, the reaction solution is poured onto 250 g of ice, saturated with 80 g of sodium chloride and extracted 3× with 150 ml of ethyl methyl ketone. The combined org. phases are extracted with 100 ml of sat. NaCl solution, dried over sodium sulfate, and the solvent is removed in vacuo. Crystallisation from ethyl acetate gives the product as a white solid.

Example 6

Synthesis of 2,4,6-triiodo-3-aminoacetylbenzoic acid O-ascorbate [2-(3,4-dihydroxy-5-oxo-2,5-dihydrofuran-2-yl)-2-hydroxyethyl 3-acetylamino-2,4,6-triiodobenzoate]

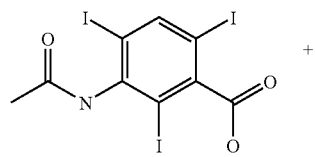

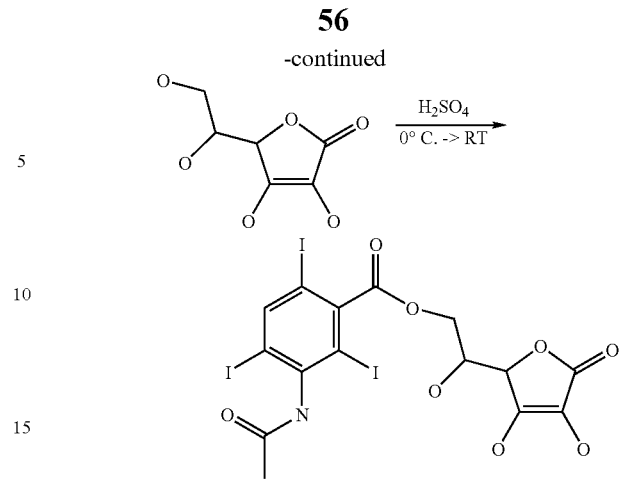

50 ml of conc. sulfuric acid are initially introduced in an argon-flushed 3-necked flask and cooled to 0° C. 14.05 g (79.8 mmol, 5 eq.) of ascorbic acid and subsequently 8.89 g of 2,4,6-triiodo-3-aminoacetylbenzoic acid (15.96 mmol, 1 eq.) are added in portions. After a reaction time of 16 hrs. at room temperature, the reaction solution is poured onto 250 g of ice, saturated with 80 g of sodium chloride and extracted 3× with 150 ml of ethyl methyl ketone. The combined org. phases are extracted with 100 ml of sat. NaCl solution, dried over sodium sulfate, and the solvent is removed in vacuo. Crystallisation from ethyl acetate gives the product as a white solid.

Example 7

Synthesis of para-diethylaminobenzoic acid 6-O-ascorbate

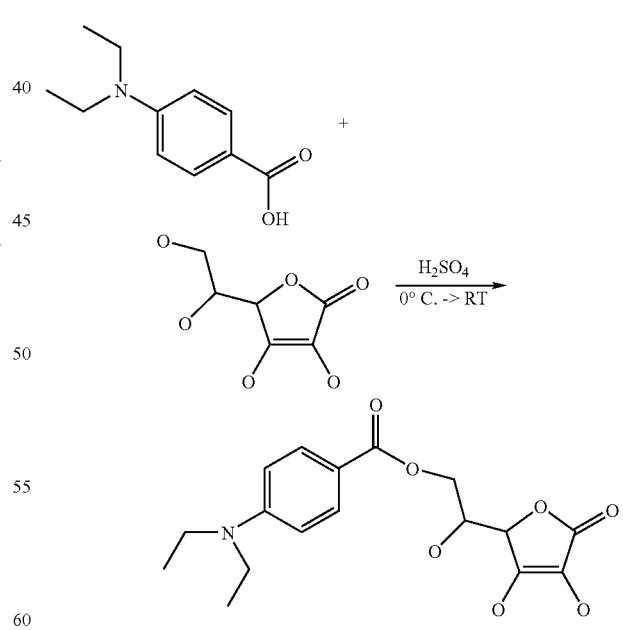

40 ml of conc. sulfuric acid are initially introduced in an argon-flushed 3-necked flask and cooled to 0° C. 11.39 g (64.69 mmol, 5 eq.) of ascorbic acid and subsequently 2.5 g of para-diethylaminobenzoic acid (12.94 mmol, 1 eq.) are added in portions. 8 ml of oleum (sulfuric acid containing 65% of $SO_3$) are then added dropwise. After a reaction time of 16 hrs.

at 60° C., the reaction solution is poured onto 120 g of ice, saturated with 60 g of sodium chloride and extracted 3× with 100 ml of ethyl methyl ketone. The combined org. phases are extracted with 80 ml of sat. NaCl solution, dried over sodium sulfate, and the solvent is removed in vacuo. Crystallisation from ethyl acetate gives the product as a solid.

In this reaction procedure, the compound para-diethylaminobenzoic acid 5-O-ascorbate also forms as a consequence of the synthesis. The proportion of this compound in the mixture is between 0 and 25%.

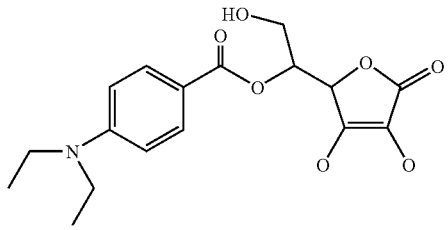 [SMILES: CCN(CC)c1ccc(C(=O)OC(CO)C2OC(=O)C(O)=C2O)cc1]

para-Diethylaminobenzoic acid 5-ascorbate

Example 8

Synthesis of (R)-2-((R)-3,4-dihydroxy-5-oxo-2,5-dihydrofuran-2-yl)-2-hydroxyethyl 3-benzotriazol-2-yl-4-hydroxybenzoate

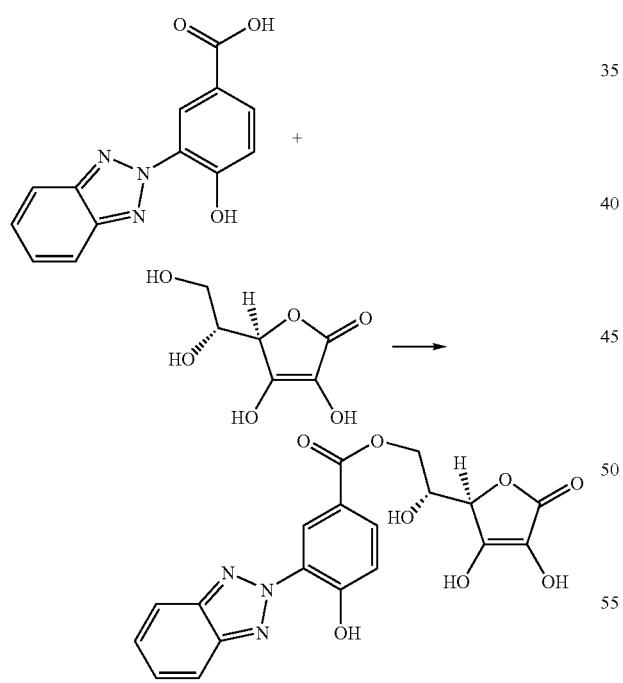

265 ml of conc. sulfuric acid are initially introduced in an argon-flushed 3-necked flask and cooled to 0° C. 124.2 g (0.705 mol, 3 eq.) of ascorbic acid and subsequently 60 g of 3-benzotriazol-2-yl-4-hydroxybenzoic acid (0.235 mol, 1 eq.) are added in portions. 73.7 ml of oleum (sulfuric acid containing 65% of SO$_3$) are then added dropwise. After a reaction time of 5 hrs. at 45° C., the reaction solution is poured onto 1000 g of ice, saturated with 200 g of sodium chloride and extracted 3× with 1000 ml of ethyl methyl ketone. The combined org. phases are extracted with 500 ml of sat. NaCl solution, dried over sodium sulfate, and the solvent is removed in vacuo. Crystallisation from ethyl acetate gives the product as a white solid.

Example 9

Synthesis of 2-ethylhexyl(E)-3-{4-[(R)-2-((R)-3,4-dihydroxy-5-oxo-2,5-di-hydrofuran-2-yl)-2-hydroxyethoxy]phenyl}acrylate

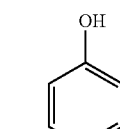

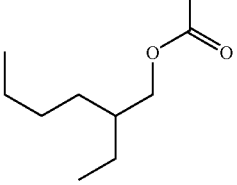

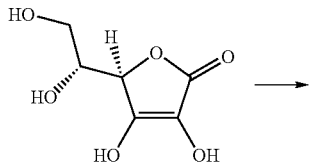

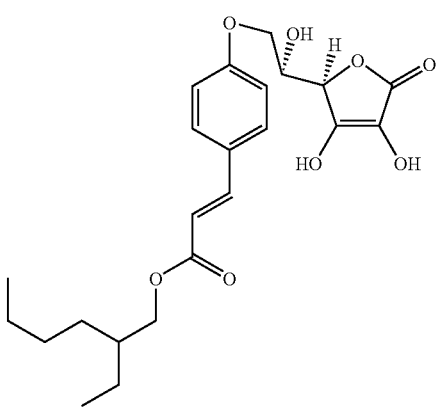

20 g of ascorbic acid (113.5 mmol; 1 eq.) are dissolved in 100 ml of di-methylformamide in an argon-flushed 3-necked flask, 32.76 g of triphenyl-phosphine are added, and 25.3 g of diisopropyl azodicarboxylate (124.9 mmol; 1.1 eq) are slowly added dropwise at 0° C. After 30 min, the 2-ethylhexyl (E)-3-(4-hydroxyphenyl)acrylate (32.95 g; 1.05 eq; 119.2 mmol) dissolved in 45 ml of dimethylformamide is added dropwise. After 30 min at 0° C., the mixture is stirred at room temperature for a further 6 hrs. The reaction solution is evaporated to dryness, suspended in 100 ml of ethyl acetate/hexane 1:2, filtered, and the product is precipitated as a white solid by addition of 100 ml of hexane.

Example 10

Synthesis of (R)-2-((R)-3,4-dihydroxy-5-oxo-2,5-dihydrofuran-2-yl)-2-hydroxyethyl 2-phenyl-3H-benzimidazole-5-sulfonate

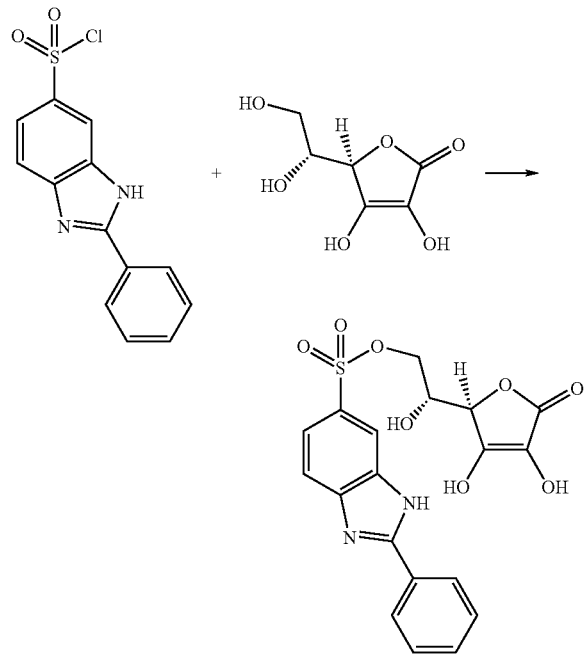

45.1 g of ascorbic acid (255.2 mmol; 3 eq.) are dissolved in 100 ml of DMF, 521 mg of 4-dimethylaminopyridine (4.27 mmol; 0.05 eq.) are added, and 25 g of 2-phenyl-3H-benzimidazole-5-sulfonyl chloride (85.4 mmol; 1 eq.), dissolved in 66 ml of DMF, are added dropwise at 0° C. The mixture is subsequently warmed to room temperature, and, after 6 hrs., 100 ml of water and 100 ml of chloroform are added, the mixture is extracted, dried, and the solvent is removed in vacuo. The residue is recrystallised from toluene, giving the product as a pale-beige solid.

Example 11

Synthesis of (R)-5-[(R)-2-(3-benzotriazol-2-yl-4-hydroxybenzyloxy)-1-hydroxyethyl]-3,4-dihydroxy-5H-furan-2-one

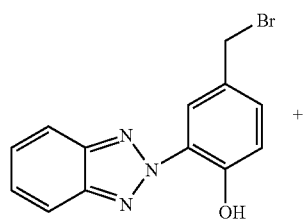

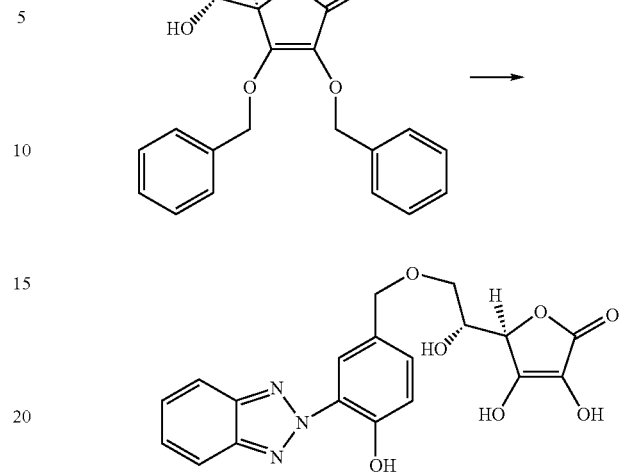

35 g of (R)-3,4-bisbenzyloxy-5-((R)-1,2-dihydroxyethyl)-5H-furan-2-one (98.2 mmol; 1 eq.) are dissolved in 250 ml of THF under a protective-gas atmosphere, and 3.93 g of sodium hydroxide (98.2 mmol; 1 eq.) are added at 0° C. After 30 min, the 2-benzotriazol-2-yl-4-bromomethylphenol (35.8 g; 117.9 mmol; 1.2 eq.) dissolved in 100 ml of THF is added dropwise, the mixture is stirred at 0° C. for 60 min and at 70° C. for 7 hours. After the reaction solution has been cooled to room temperature, 2 g of Pd/C are added, and the mixture is hydrogenated for 5 hours under a hydrogen atmosphere at 3 bar and 50° C. After filtration through a Celite pad, the solution is neutralised using 2 N HCl solution. The extraction is carried out twice with 250 ml of sat. NaHCO₃ solution and 100 ml of sat. NaCl solution. The product is precipitated from the org. phase using 370 ml of heptane.

Example 12

Synthesis of (R)-2-((R)-3,4-dihydroxy-5-oxo-2,5-dihydrofuran-2-yl)-2-hydroxyethyl 5-((3aR,6S,6aS)-2-oxohexahydrothieno[3,4-d]imidazol-6-yl)-pentanoate

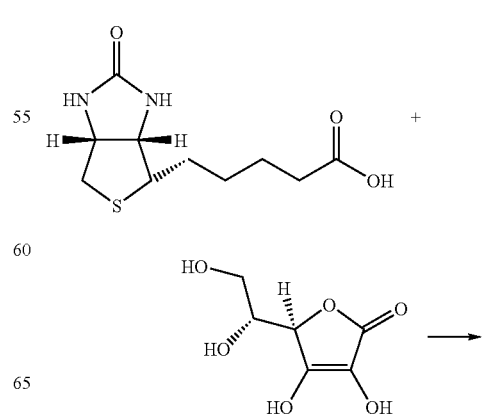

-continued

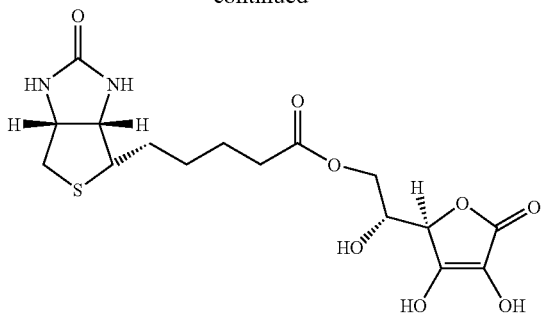

54.1 g of ascorbic acid (306.9 mmol; 5 eq.) and 15 g of biotin (61.4 mmol; 1 eq.) are dissolved in 180 ml of anhydrous acetone under a protective gas, 1 g of lipase (*Candida antarctica*) is added, and the mixture is shaken at 40° C. for 32 h. The enzyme is filtered off, 50 ml of water are added to the solution, and the product is precipitated by pouring into toluene.

Evidence of Bonding:

Example I

Evidence of Bonding (Skin Model)

4% solutions of a mixture of two isomers of 2-(3,4-dihydroxy-5-oxo-2,5-di-hydrofuran-2-yl)-2-hydroxyethyl 2-(4-diethylamino-2-hydroxybenzoyl)benzo-ate, prepared in accordance with Example 1 or 2, abbreviated to DHAB below, in various solvent systems are prepared. 40 □l of each of these are applied to 2.5×7.5 cm gelatine plates and stored at 87% atmospheric humidity for 24 hrs. The plates are then eluted with 50 ml of iPrOH in an ultrasound bath for 5 min. The bonding to the gelatine is carried out by comparison with a corresponding standard solution:

TABLE 1

| Sample | Solvent | Non-extractable content and therefore bonded to the skin |
|---|---|---|
| 1 | i-PrOH | 12.5% |
| 2 | EG/water 94/6 | 97.0% |

DHAB also denotes Diethylamino Hydroxybenzoyl Ascorbyl Benzoate. DHHB below denotes Diethylamino Hydroxybenzoyl Hexyl Benzoate, a non-bonding UV filter, known as Uvinul® A Plus.

Example II

Evidence of Bonding to Chicken Skin

A) DHAB is dissolved to the extent of 2% in dimethylisosorbide. The solution is applied to chicken skin at an application rate of 2.66 μl/cm². After an exposure time of 16 hours, the samples are extracted with isopropanol in an ultrasound bath. The extracts are measured photometrically at 354 nm and compared with a 100% value (=application solution without use). The difference in the recovery compared with the 100% value corresponds here to the proportion of active compound bonded to the skin. For DHAB, a bound proportion of 76% is found, while the non-bonding comparative substance DHHB has, as expected, a low value of only 3%.

B) Evidence of bonding to pig skin:
The following materials are prepared:
2% solution of DHAB in Arlasolve DMI sample (A) and Pelemol BIP sample (B)
formulation containing 1% of DHAB sample (C) [=54-07-5-A, from Example V]
2% solution of DHHB in Arlasolve DMI sample (D) and isopropyl myristate sample (E)
formulations containing 0.84% of DHHB sample (F) [=54-07-5-B from Example V] and 0.84% of DHHB+0.37% of vitamin C sample (G) [=54-07-5-C from Example V].
pig skin is cut to 2.5×7.5 cm and placed on Plexiglas specimen slides.

Procedure:
50 □l of each of samples (A) to (G) are dripped onto the specimen slides with pig skin, spread using a plastic spatula, and the specimen slides are stored in a desiccator [87% atmospheric humidity through sat. KCl solution] at room temperature for 24 h. The specimen slides are then rinsed with 50 ml of isopropanol into volumetric flasks, treated in an ultrasound bath for 5 min, clear-filtered via syringe filters (cloudiness due to detached skin constituents and measured by UV spectrometer (400-250 nm; $UV_{max}$~355 nm) (residue 1 to 7). The 100% comparative value used are 50 ml isopropanol solutions of in each case 50 □l of samples (A) to (G), which are likewise measured by UV spectrometer.

The results are summarised in Table 2:

| Active compound | Content | abs (~355 nm) | Bonding* |
|---|---|---|---|
| Residue | | | |
| 1 DHAB | 2% in Arlasolve DMI | 0.047 | 97% |
| 2 DHAB | 2% in Pelemol BIP | 0.152 | 89% |
| 3 DHAB | 1% in W/O 54-07-5-A | 0.042 | 91% |
| 4 DHHB | 2% in Arlasolve DMI | 2.013 | 0% |
| 5 DHHB | 2% in isopropyl myristate | 1.477 | 2% |
| 6 DHHB | 0.84% in W/O 54-07-5-B | 0.691 | 5% |
| 7 DHHB + vitamin C | 0.84% + 0.37% in W/O 54-07-5-C | 0.719 | 8% |
| 100% comparative values (=direct measurement without application to pig skin) | | | |
| Sample | | | |
| A DHAB | 2% in Arlasolve DMI | 1.501 | |
| B DHAB | 2% in Pelemol BIP | 1.375 | |
| C DHAB | 1% in W/O 54-07-5-A | 0.459 | |
| D DHHB | 2% in Arlasolve DMI | 2.023 | |
| E DHHB | 2% in isopropyl myristate | 1.504 | |
| F DHHB | 0.84% in W/O 54-07-5-B | 0.730 | |
| G DHHB + vitamin C | 0.84% in W/O 54-07-5-C | 0.781 | |

*The term "bonding" is equivalent to the term "non-extractable residue". The extraction was carried out with isopropanol. The samples were additionally treated with ultrasound for 5 min.

Example III

Evidence of Bonding to Hair

Human hair samples are stirred with a 0.2% ethanolic active-compound solution of DHAB or DHHB (ethanol/water=80/20) for 8 h, subsequently rinsed with ethanol/water=80/20 and sent for SEM measurement (SEM=scanning electron microscope). The comparison between DHAB and DHHB shows that regions which are interpreted as active-compound adduction onto the hair cuticles are clearly increasingly evident in the DHAB SEM picture.

Example IV

Antioxidative Efficacy

The basis for the determination of the antioxidative efficacy is the so-called DPPH test, as described in Bünger et. al. [Buenger, J., Ackermann, H., Jentzsch, A., Mehling, A., Pfizner, I., Reiffen, K.-A., Schroeder, K.-R., and Wollenweber U., An interlaboratory comparison of methods used to assess antioxidant potentials, *Int. J. Cosm. Sci.*, 28 (2006) 1-12]. The antioxidative efficacy of DHAB is determined in the DPPH test. The EC50 value for DHAB is 0.32 µmol/l and reflects the excellent free-radical scavenger properties of DHAB. This is comparable with ascorbic acid itself, whose value is determined as 0.29 µmol/l. DHHB gives only 36 µmol/l and can be referred to as DPPH-inactive.

Formulations for cosmetic compositions are described by way of example below:

Example V

W/O Emulsion

|  | 54-07-5-A | 54-07-5-B | 54-07-5-C | 54-07-5-D | 54-07-5-E |
|---|---|---|---|---|---|
| Cetyl PEG/PPG-10/1 dimethicone (Abil EM 90) | 3.00 | 3.00 | 3.00 | 3.00 | 3.00 |
| Polyglyceryl-4 isostearate (Isolan GI 34) | 1.50 | 1.50 | 1.50 | 1.50 | 1.50 |
| Butylphthalimide iso-propylphthalimide (Pelemol ® BIP) | 5.00 | 5.00 | 5.00 | 5.00 | 5.00 |
| Dimethyl isosorbide (Arlasolve DMI) | 5.00 | 5.00 | 5.00 | 5.00 | 5.00 |
| DHAB | 1.00 |  |  | 1.00 | 2.00 |
| Uvinul ® A Plus (DHHB) |  | 0.84 | 0.84 | 1.00 |  |
| Ascorbic acid |  |  | 0.37 | 1.00 | 3.00 |
| Mineral Oil | 8.00 | 8.00 | 8.00 | 8.00 | 8.00 |
| Ethylhexyl stearate (Tegosoft ® OS) | 5.00 | 5.00 | 5.00 | 5.00 | 5.00 |
| Cyclomethicone (and) Aluminium/Magnesium Hydroxide Stearate (Gilugel SIL 5) | 5.00 | 5.00 | 5.00 | 5.00 | 5.00 |
| Preservative | 1.00 | 1.00 | 1.00 | 1.00 | 1.00 |
| Water | to 100 | to 100 | to 100 | to 100 | to 100 |
| NaCl | 0.50 | 0.50 | 0.50 | 0.50 | 0.50 |
| EDTA | 0.10 | 0.10 | 0.10 | 0.10 | 0.10 |
| Citric acid q.s. |  |  |  |  |  |

Preparation: Pelemol® BIP, Arlasolv DMI and emulsifiers are initially introduced. DHAB and Uvinul® A Plus are dissolved therein. The remaining constituents of the oil phase are added and mixed homogeneously. The water phase, adjusted to pH=4-5, is emulsified in with stirring. The mixture is subsequently homogenised. The emulsions can be prepared under gentle conditions at room temperature. DHAB can be stabilised by increasing the content of ascorbic acid. The preparation is ideally prepared with inertisation (exclusion of oxygen).

Example VI

Water-Resistant Sunscreen Spray

| A |  |  |  |
|---|---|---|---|
| DHAB | 1.00 | 1.00 | 2.00 |
| Diethylhexyl Syringylidenemalonate, Caprylic/Capric Triglyceride (Oxynex ® ST liquid) |  | 0.50 |  |
| RonaCare ® AP |  | 2.00 |  |
| Ascorbyl Palmitate |  |  | 1.00 |
| Cyprylic/capric Triglyceride (Miglyol 812 N) | 7.00 | 7.00 | 7.00 |
| Butylphthalimide isopropylphthalimide (Pelemol ® BIP) | 10.00 | 10.00 | 10.00 |
| C12-15 alkyl benzoate (Tegosoft ® TN) | 10.00 | 10.00 | 10.00 |
| Phenethyl benzoate (X-Tend 226) | 5.00 | 5.00 | 5.00 |
| RonaCare ® tocopherol acetate | 1.00 | 1.00 | 1.00 |
| B |  |  |  |
| Cyclopentasiloxane (Dow Corning 245) | 43.80 | 41.30 | 41.80 |
| Phenyltrimethicone (Dow Corning 556) | 2.00 | 2.00 | 2.00 |
| Cyclopentasiloxane, dimethiconol Dow Corning 1501 Fluid | 20.00 | 20.00 | 20.00 |
| Perfume oil (q.s.) | 0.20 | 0.20 | 0.20 |

Preparation: the components of phase A are combined at room temperature and stirred until a clear solution is present. Phase B is subsequently mixed and added to phase B with stirring. Stirring is continued until finally the clear product is present. The stability of the substances according to the invention can be increased by addition of antioxidants, such as Oxynex® ST liquid, RonaCare® AP or ascorbyl palmitate.

Example VII

Pump Hairspray

| A |  |  |  |
|---|---|---|---|
| DHAB | 1.00 | 2.00 | 4.00 |
| Ethanol 96% extra pure | to 100 | to 100 | to 100 |
| PVP/VA copolymer PVP/VA W 735 | 6.00 | 6.00 | 6.00 |
| B |  |  |  |
| Diethylhexyl Syringylidenemalonate, Caprylic/Capric Triglyceride (Oxynex ® ST liquid) | 0.06 | 0.25 | 0.50 |
| PEG-75 lanolin BHT (Solan E - low dioxane) | 0.20 | 0.20 | 0.20 |
| Perfume (Frag 280853 Green Activating) | 0.10 | 0.10 | 0.10 |
| C |  |  |  |
| Water, demineralised | 13.00 | 13.00 | 13.00 |
| Titriplex III | 0.10 | 0.10 | 0.10 |

| | | | |
|---|---|---|---|
| PEG-12 dimethicone Dow Corning 193 fluid | 0.50 | 0.50 | 0.50 |
| 0.1% of D&C Red No 33 (CI 17200) in water | 0.20 | 0.20 | 0.20 |
| PEG-40 Hydrogenated Castor Oil (Cremophor RH 410) | 1.00 | 1.00 | 1.00 |

Preparation: pre-dissolve phase A until a clear solution is present. Add phase B to phase A with stirring. Pre-mix phase C and add to the remainder, stir until a homogeneous mixture has formed.

Example VIII

W/O Emulsions

| Emulsion | A | B | C | D | E | F |
|---|---|---|---|---|---|---|
| Polyglyceryl 2-dipolyhydroxystearate | 3 | 5 | 3 | | | |
| PEG-30 dipolyhydroxystearate | | | 2 | 3 | 4 | 5 |
| Sodium starch octenylsuccinate | 0.5 | 0.4 | | 0.3 | | 1 |
| Glycine | 0.3 | 0.3 | 0.5 | 0.4 | | |
| Alcohol | | 5 | 2 | 5 | 4 | |
| Magnesium sulfate | 0.2 | 0.3 | 0.3 | 0.4 | 0.5 | 0.2 |
| $C_{12-15}$ alkyl benzoate | 5 | 3 | | | 5 | |
| $C_{12-13}$ alkyl tartrate | | 2 | | | | |
| Butylene glycol dicaprylate/dicaprate | 5 | | | | 3 | 3 |
| Dicaprylyl ether | | | | | 2 | |
| Mineral oil | | 4 | | 6 | | 8 |
| Octyldodecanol | 2 | | | | | |
| Dicaprylic caprate | | 2 | | | 2 | 2 |
| Cyclomethicone | 5 | | 5 | 10 | | |
| Dimethicone | | | | 5 | | |
| Isohexadecane | | 1 | | | | |
| Butylene glycol | 5 | 8 | | | | 3 |
| Propylene glckol | | | 1 | | 5 | 3 |
| Glycerine | 3 | 5 | 7 | 10 | 3 | 3 |
| C18-38 acid triglycerides | 0.5 | | 1 | | 1 | |
| Titanium dioxide | 5 | 6 | 4 | | | 4 |
| Zinc oxide | 5 | | | | | |
| Bisethylhexyloxyphenol-methoxyphenyltriazine | | 3 | 3 | 2 | | |
| Ethylhexyltriazone | | 4.5 | 3 | | 3 | |
| DHAB | 2.0 | 0.5 | 1.0 | 1.0 | 3.0 | 1.5 |
| Diethylhexylbutamidotriazone | | | 1.5 | 4 | | |
| Butylmethoxydibenzoylmethane | 2 | 3 | 4 | | 1 | 3 |
| Uvinul ® A Plus | | | | 4 | 2 | |
| Ethylhexyl methoxycinnamate | | | | | 7 | 5 |
| DHAB coupled to gelatine | 1.5 | 5.5 | | 8.0 | 4.5 | 7.5 |
| Benzotriazole coupled to gelatine | 4 | | 6 | | | |
| Taurine | 0.1 | | | 0.5 | 0.2 | |
| Vitamin E acetate | 0.2 | 02 | | 0.3 | 0.1 | 0.5 |
| $Na_2H_2EDTA$ | 0.1 | 0.1 | 0.2 | 0.2 | 0.2 | 0.5 |
| C8-C16 alkylpolyglycoside | 1 | | | | | |
| Perfume, preservatives | q.s. | q.s | q.s | q.s | qs. | qs. |
| Dyes, etc. | q.s. | q.s. | q.s. | q.s | q.s. | q.s. |
| Sodium hydroxide | q.s. | q.s. | q.s. | q.s | q.s. | q.s. |
| Water | to 100.0 | to 100.0 | to 100.0 | to 100.0 | to 100.0 | to 100.0 |

Example IX

Hair-Care Formulation

| | Content in g of component per 100 g of formulation | | | | | |
|---|---|---|---|---|---|---|
| Component | A | B | C | D | E | F |
| Disodium EDTA | 0.100 | 0.100 | 0.100 | 0.100 | 0.100 | 0.100 |
| Oxynex ® ST | 2.000 | 2.000 | 2.000 | 2.000 | 2.000 | 2.000 |
| DHAB | 0.10 | 0.25 | 0.50 | 1.50 | 2.00 | 4.00 |
| Hexamidine diisethionate | 0.100 | 0 | 0 | 0 | 0 | 0 |
| Tetrahydrocurcumin | 0 | 0.500 | 0 | 0 | 0 | 0 |
| Glycyrrhetinic acid | 0 | 0 | 0.300 | 0 | 0 | 0 |
| Thiotaine ®[1] | 0 | 0 | 0 | 5.000 | 0 | 0 |

-continued

| Content in g of component per 100 g of formulation | | | | | | |
|---|---|---|---|---|---|---|
| Component | A | B | C | D | E | F |
| N-undecylenoyl-L-phenyl-alanine | 0 | 0 | 0 | 0 | 1.000 | 0 |
| N-acetylglucosamine | 0 | 0 | 0 | 0 | 0 | 2.000 |
| Niacinamide | 5.000 | 5.000 | 5.000 | 5.000 | 5.000 | 5.000 |
| Citric acid | 0.015 | 0 | 0 | 0 | 0 | 0 |
| Isohexadecane | 3.000 | 3.000 | 3.000 | 3.000 | 3.000 | 3.000 |
| Isopropyl isostearate | 1.330 | 1.330 | 1.330 | 1.330 | 1.330 | 1.330 |
| Isopropyl N-laurosyl-sarcosinate | 0 | 0 | 5.000 | 0 | 0 | 0 |
| Sucrose polycottonseedate | 0.670 | 0.670 | 0.670 | 0.670 | 0.670 | 0.670 |
| Polymethylsilsesquioxane | 0.250 | 0.250 | 0.250 | 0.250 | 0.250 | 0.250 |
| Cetearyl glucoside + cetearyl alcohol | 0.200 | 0.200 | 0.200 | 0.200 | 0.200 | 0.200 |
| Behenyl alcohol | 0.400 | 0.400 | 0.400 | 0.400 | 0.400 | 0.400 |
| Ethylparaben | 0.200 | 0.200 | 0.200 | 0.200 | 0.200 | 0.200 |
| Propylparaben | 0.100 | 0.100 | 0.100 | 0.100 | 0.100 | 0.100 |
| Cetyl alcohol | 0.320 | 0.320 | 0.320 | 0.320 | 0.320 | 0.320 |
| Stearyl alcohol | 0.480 | 0.480 | 0.480 | 0.480 | 0.480 | 0.480 |
| Tocopheryl acetate | 0.500 | 0.500 | 0.500 | 0.500 | 0.500 | 0.500 |
| PEG-100 stearate | 0.100 | 0.100 | 0.100 | 0.100 | 0.100 | 0.100 |
| Glycerine | 7.000 | 7.000 | 7.000 | 7.000 | 7.000 | 7.000 |
| Titanium dioxide | 0.604 | 0.604 | 0.604 | 0.604 | 0.604 | 0.604 |
| Polyacrylamide + C13-14 isoparaffin + laureth-7 | 3.000 | 2.000 | 2.000 | 2.000 | 2.000 | 2.000 |
| Panthenol | 1.000 | 1.000 | 1.000 | 1.000 | 1.000 | 1.000 |
| Benzyl alcohol | 0.400 | 0.400 | 0.400 | 0.400 | 0.400 | 0.400 |
| Dimethicone + dimethiconol | 2.000 | 2.000 | 2.000 | 2.000 | 2.000 | 2.000 |
| Water (to 100 g) | to 100 | to 100 | to 100 | to 100 | to 100 | to 100 |
| TOTAL | 100 | 100 | 100 | 100 | 100 | 100 |

Example X

Hair-Care Formulation

| Content in g of component per 100 g of formulation | | | |
|---|---|---|---|
| Component | G | H | I |
| Disodium EDTA | 0.100 | 0.100 | 0.100 |
| Oxynex ® ST | 2.000 | 2.000 | 2.000 |
| DHAB | 0.50 | 3.50 | 1.50 |
| Cetylpyridinium chloride | 0.200 | 0 | 0 |
| Pitera ® | 0 | 10 | 0 |
| Ascorbyl glycoside | 0 | 0 | 2.000 |
| Niacinamide | 5.000 | 5.000 | 5.000 |
| Polyquaternium 37 | 0 | 0 | 0 |
| Isohexadecane | 3.000 | 3.000 | 3.000 |
| Isopropyl isostearate | 1.330 | 1.330 | 1.330 |
| Sucrose polycottonseedate | 0.670 | 0.670 | 0.670 |
| Polymethylsilsesquioxane | 0.250 | 0.250 | 0.250 |
| Cetearyl glucoside + cetearyl alcohol | 0.200 | 0.200 | 0.200 |
| Behenyl alcohol | 0.400 | 0.400 | 0.400 |
| Ethylparaben | 0.200 | 0.200 | 0.200 |
| Propylparaben | 0.100 | 0.100 | 0.100 |

-continued

| Content in g of component per 100 g of formulation | | | |
|---|---|---|---|
| Component | G | H | I |
| Cetyl alcohol | 0.320 | 0.320 | 0.320 |
| Stearyl alcohol | 0.480 | 0.480 | 0.480 |
| Tocopheryl acetate | 0.500 | 0.500 | 0.500 |
| PEG-100 stearate | 0.100 | 0.100 | 0.100 |
| Glycerine | 7.000 | 7.000 | 7.000 |
| Titanium dioxide | 0.604 | 0.604 | 0.604 |
| Polyacrylamide + C13-14 isoparaffin + laureth-7 | 2.000 | 2.000 | 2.000 |
| Panthenol | 1.000 | 1.000 | 1.000 |
| Benzyl alcohol | 0.400 | 0.400 | 0.400 |
| Dimethicone + dimethiconol | 2.000 | 2.000 | 2.000 |
| Water (to 100 g) | to 100 | to 100 | to 100 |
| TOTAL | 100 | 100 | 100 |

Example XI

O/W Emulsions

| Emulsion | A | B | C | D | E | F |
|---|---|---|---|---|---|---|
| Glyceryl stearate citrate | 2.5 | 2 | 3 | | | |
| Sorbitan stearate | 0.5 | | | 2 | 1.5 | 2 |
| Polyglyceryl-3 methylglucose distearate | | | | 2.5 | 3 | 3 |
| Polyglyceryl-2 dipolyhydroxystearate | | 0.8 | | | | 0.5 |
| Cetearyl alcohol | | | 1 | | | |
| Stearyl alcohol | 2 | | | | | 2 |
| Cetyl alcohol | | 1 | | | 3 | |

-continued

| Emulsion | A | B | C | D | E | F |
|---|---|---|---|---|---|---|
| Acrylates/$C_{10-30}$ alkyl acrylate crosspolymer | | 0.2 | | | 0.1 | |
| Carbomer | | 0.2 | 0.3 | 0.2 | | |
| Xanthan gum | 0.4 | | 0.2 | 0.2 | 0.3 | 0.4 |
| $C_{12-15}$ alkyl benzoate | 5 | 3 | | | 5 | |
| $C_{12-13}$ alkyl tartrate | | 2 | | | | |
| Butylene glycol dicaprylat/dicaprat | 5 | | | | 3 | 3 |
| Dicaprylyl ether | | | | | 2 | |
| Octyldodecanol | 2 | | | | | |
| Dicapryl caprate | | 2 | | | 2 | 2 |
| Cyclomethicone | 5 | | 5 | 10 | | |
| Dimethicone | | | | 5 | | |
| Isohexadecane | | 1 | | | | |
| Butylene glycol | 5 | 8 | | | | 3 |
| Propylene gycol | | | 1 | | 5 | 3 |
| Glycerine | 3 | 5 | 7 | 10 | 3 | 3 |
| C18-C38 acid triglyceride | 0.5 | | 1 | | 1 | |
| Titanium dioxide | 5 | | | 2 | | |
| 2.2'-Methylenebis(6-(2H-benzotriazol-2-yl)-(1,1,3,3-tetramethylbutyl)phenol) | 2.5 | | | | | |
| 2,4,6-Tris(biphenyl)-1,3,5-triazine | | 2 | | | | |
| Merocyanine coupled to gelatine | 6 | | 6 | | 10 | 3 |
| Benzotriazole coupled to gelatine | | 5 | | 10 | | 3 |
| C8-C16 alkylpolyglycoside | 1 | 0.6 | | | | |
| UVASorb ® K2A | | | 2 | | | |
| Uvinul ® A Plus | 2 | | | | | 1 |
| Homosalate | | 5 | | 1 | | |
| Phenylbenzimidazolesulfonic acid | | | 2 | | | 1 |
| Benzophenone-3 | 2 | | | | 2 | |
| Octyl salicylate | 5 | 5 | | 2 | | |
| Octocrylene | 2 | | | | 3 | 1 |
| DHAB | 1.0 | 2.0 | 3.0 | 1.0 | 2.0 | 3.0 |
| Bisethylhexyloxyphenol-methoxyphenyltriazine | | 3 | 2 | 1 | | |
| Parsol ® SLX | | | 3 | | | |
| Dihydroxy acetate | | | | | 4 | |
| Taurine | 0.1 | | | 0.5 | 0.2 | |
| 8-Hexadecene-1,16-dicarboxylic acid | | 0.2 | | | | |
| Vitamin E acetate | 0.2 | 0.2 | | 0.3 | 0.1 | 0.5 |
| $Na_2H_2EDTA$ | 0.1 | 0.1 | 0.2 | 0.2 | 0.2 | 0.5 |
| Perfume, preservatives | q.s. | q.s. | q.s. | q.s. | q.s. | q.s. |
| Dyes, etc. | q.s. | q.s. | q.s. | q.s. | q.s. | q.s. |
| Sodium hydroxide | q.s. | q.s. | q.s. | q.s. | q.s. | q.s. |
| Water | to 100.0 | to 100.0 | to 100.0 | to 100.0 | to 100.0 | to 100.0 |

Example XII

O/W Emulsions

| Emulsion | G | H | I | K | L | M |
|---|---|---|---|---|---|---|
| Ceteareth-20 | 1 | 1.5 | 1 | | 0.5 | |
| Sorbitan stearate | | | 0.5 | | | |
| Glyceryl stearate SE | | | | 1 | 1 | 1.5 |
| Emulgade F ® | | | | 2.5 | 2.5 | 3 |
| Cetearyl alcohol | | | | 1 | | |
| Stearyl alcohol | | | | | 1.5 | |
| Cetyl alcohol | | | 0.5 | | | 2 |
| Acrylates/$C_{10-30}$ alkyl acrylate crosspolymer | 0.2 | 0.4 | 0.3 | 0.1 | | |
| Carbomer | | | | | 0.3 | |
| Xanthan gum | | | | 0.4 | | 0.4 |
| $C_{12-15}$ alkyl benzoate | 5 | 3 | | | 5 | |
| 2-Phenyl benzoate | | 2 | | | | |
| Butylene glycol dicaprylat/dicaprat | 5 | | | | 3 | 2 |

-continued

| Emulsion | G | H | I | K | L | M |
|---|---|---|---|---|---|---|
| Dicaprylyl ether | | | | | 2 | |
| Diethylhexyl naphthalate | 2 | | | | | |
| Dicapryl caprate | | 2 | | | 2 | 2 |
| Cyclomethicone | 5 | | 5 | 10 | | |
| Isohexadecane | | | | 5 | | |
| Mineral oil | | 1 | | | | |
| Propylene glycol | | | 4 | | | |
| Glycerine | 5 | 7 | 3 | 5 | 6 | 8 |
| C18-38 acid triglyceride | 0.5 | | 1 | | 1 | |
| Titanium dioxide | 5 | | 3 | 2 | | |
| NeoHeliopan ® AP | | 2 | | | 1 | 1 |
| Phenylbenzimidazolesulfonic acid | 1 | | | 1 | 2 | 1 |
| Ethylhexyl methoxycinnamate | 5 | | 4 | 4 | | |
| Ethylhexyltriazone | | 2 | | 1 | | |
| Diethylhexylbutamido-triazane | 1 | | | | | |
| Butylmethoxydibenzoyl-methane | 2.5 | | 2 | 2 | | 1 |
| Bisethylhexyloxyphenol-methoxyphenyltriazine | 2 | | | | | |
| 4-Methylbenzylidene-camphor | 3 | | | | | |
| Parsol ® SLX | | | | | 2 | |
| DHAB | 1.0 | 2.0 | 4.0 | 0.5 | 1.5 | 3.0 |
| Creatinin | 0.1 | 0.01 | 0.05 | | | |
| Creatin | 0.5 | 0.2 | 0.1 | | | |
| Licorice extract/licochalcone | | | | 0.5 | | |
| Vitamin E acetate | 0.2 | | | 0.5 | 0.5 | 0.5 |
| Tapioca starch | | 3 | | | 2 | |
| Na₂H₂EDTA | 0.1 | | 0.2 | | | 0.5 |
| Perfume, preservatives | q.s. | q.s. | q.s. | q.s. | q.s. | q.s. |
| Dyes, etc. | q.s. | q.s. | q.s. | q.s. | q.s. | q.s. |
| Sodium hydroxide | q.s. | q.s. | q.s. | q.s. | q.s. | q.s. |
| Water | to 100.0 | to 100.0 | to 100.0 | to 100.0 | to 100.0 | to 100.0 |

Example XIII

O/W Emulsions

| Emulsion | N | O | P | Q | R | S |
|---|---|---|---|---|---|---|
| Glyceryl stearate SE | | 2 | | 2 | | |
| Glyceryl stearate | 2 | | 2 | | | |
| PEG-40 stearate | | | 2 | | 1 | |
| PEG-10 stearate | | | 2.5 | 1 | | |
| Ceteareth-20 | | | | | | 2.6 |
| Sodium cetyl phosphate | | | | 2 | | |
| Glyceryl stearate, ceteareth-12, ceteareth-20, cetearyl alcohol, cetyl palmitate | | | | | | 5.4 |
| Stearic acid | 3 | 2 | | | 2 | |
| Stearyl alcohol | | 2 | 2 | | | |
| Stearyl alcohol | 0.5 | | 2 | | | |
| Cetyl alcohol | 3 | | | 2 | | |
| Acrylates/C₁₀₋₃₀ alkyl acrylate crosspolymer | | | 0.2 | | 0.4 | |
| Carbomer | | 0.3 | | 0.3 | 0.3 | |
| Xanthan gum | | 0.3 | 0.4 | | | |
| C₁₂₋₁₅ alkyl benzoate | 5 | | | | 5 | 3 |
| 2-Phenyl benzoate | 5 | | | | | |
| Butylene glycol dicaprylate/dicaprate | | | 5 | 4 | | 3 |
| Dicaprylyl ether | | 2 | | 3 | | |
| Diethylhexyl naphthalate | 3 | | | | | |
| Cyclomethicone | 2 | | 10 | 2 | | |
| Isohexadecane | | | | 2 | 3 | |
| Mineral oil | | | | | 3 | |
| Propanediol | | 3 | | 5 | | |
| Glycerine | 3 | 5 | 10 | 7 | 4 | 5 |
| Titanium dioxide | 2 | 4 | | | | |
| Zinc oxide | | | | | 2 | |
| Drometrizole trisiloxane | | | | | 3 | |
| Ethylhexyl methoxycinnamate | | | 6 | 5 | | |
| Phenylbenzimidazole-sulfonic acid | | 0.5 | 2 | | 1 | |
| Homosalate | 5 | | | 7 | | |
| Butylmethoxydibenzoyl-methane | | 3 | | | | |
| Bisethylhexyloxyphenol-methoxyphenyltriazine | | | 2 | 3 | | |
| Octyl salicylate | | | | | 5 | |
| Octocrylene | | | | | 3 | |
| DHAB | 0.25 | 1.5 | 0.5 | 2.5 | 1.0 | 5.0 |
| Parsol ® SLX | 4 | | | | | 5 |
| PVP hexadecene copolymer | 0.5 | | 1 | | 0.8 | |
| Coenzyme Q 10 | 0.2 | 0.02 | | 0.3 | | |
| Vitamin E acetate | 0.2 | | 0.3 | | 0.8 | 0.5 |
| Na₂H₂EDTA | 0.1 | | | | | 0.5 |
| Perfume, preservatives | q.s. | q.s. | q.s. | q.s. | q.s. | q.s. |
| Dyes, etc. | q.s. | q.s. | q.s. | q.s. | q.s. | q.s. |
| Sodium hydroxide | q.s. | q.s. | q.s. | q.s. | q.s. | q.s. |
| Water | to 100.0 | to 100.0 | to 100.0 | to 100.0 | to 100.0 | to 100.0 |

Example XIV

Hydrodisperions (Lotions and Sprays)

| | A | B | C | D | E | F |
|---|---|---|---|---|---|---|
| Glyceryl stearate citrate | | 0.40 | | | | |
| Cetyl alcohol | | | | | 2.00 | |
| Sodium carbomer | | | | | 0.30 | |
| Acrylates/$C_{10-30}$ alkyl acrylate crosspolymer | 0.30 | | 0.30 | 0.40 | 0.10 | 0.10 |
| Cetsareth-20 | | | 1.00 | | | |
| Xanthan gum | | | | 0.15 | | 0.50 |
| Dimethicone/vinyl-dimethicone crosspolymer | | | | 5.00 | | 3.00 |
| UVASorb ® K2A | | | | | 3.50 | |
| Uvinul ® A Plus | 0.25 | | | 0.50 | 2.00 | 1.50 |
| Butylmethoxydibenzoyl-methane | 1.20 | | 3.50 | | | |
| Bisethylhexyloxyphenol-methoxyphenyltriazine | 2.00 | 2.00 | | 0.25 | | |
| Terephthalidenedicamphorsulfonic acid | | | | | | 0.50 |
| Disodium phenyl-dibenzimidazole tetrasulfonate | | | | | | 1.00 |
| Phenylbenzimidazole-sulfonic acid | | | 2.00 | | | |
| Ethylhexyl methoxycinnamate | 5.00 | | 7.00 | | 5.00 | 8.00 |
| Diethylhexylbutamido-triazone | | | 2.00 | 2.00 | | |
| Ethylhexyltriazone | 4.00 | 3.00 | | | 4.00 | |
| Octocrylene | | | | 10.00 | | 2.50 |
| DHAB | 0.25 | 1.5 | 0.5 | 2.5 | 1.0 | 5.0 |
| $C_{12-15}$ alkyl benzoate | 2.00 | | 2.50 | | | |
| Phenethyl benzoate | 4.00 | | | 7.50 | | 5.00 |
| $C_{18-36}$ triglyceride fatty acid | | | 1.00 | | | |
| Butylene glycol dicaprylat/dicaprate | | | | | 6.00 | |
| Dicaprylyl carbonate | | 3.00 | | | | |
| Dicaprylyl ether | | 2.00 | | | | |
| Cyclomethicone | | | | 1.50 | | |
| Lanolin | | | | | 0.35 | |
| PVP hexadecene copolymer | 0.50 | | 0.50 | | 0.50 | 1.00 |
| Ethylhexyloxyglycerine | | 0.75 | | 1.00 | | 0.50 |
| Glycerine | 10.00 | 5.00 | 5.00 | | 5.00 | 15.00 |
| Butylene glycol | | 7.00 | | | | |
| Glycine soya | | | | 1.00 | | |
| Vitamin E acetate | 0.50 | 0.25 | 0.50 | 0.25 | 0.75 | 1.00 |
| α-Glycosylrutin | | | | | 0.25 | |
| Trisodium EDTA | | 1.00 | 1.00 | 0.10 | 0.20 | |
| Idopropynyl butylcarbamate | 0.20 | 0.10 | | | | 0.15 |
| Methylparaben | 0.50 | | 0.20 | | 0.15 | |
| Phenoxyethanol | 0.50 | 0.40 | 0.40 | | 1.00 | 0.60 |
| Ethanol | 3.00 | 10.00 | 4.00 | 3.50 | | 1.00 |
| Perume, dyes | q.s. | q.s. | q.s. | qs. | q.s. | q.s. |
| Water | to 100 | to 100 | to 100 | to 100 | to 100 | to 100 |
| Neutralisers (sodium hydroxide, potassium hydroxid) | qs | qs | qs | qs | qs | qs |

Example XV

Aqueous and Aqueous/Alcoholic Formulations

|  | A | B | C | D | E | F |
|---|---|---|---|---|---|---|
| Ethanol | 50 | 5 | 2 | 40 | 15 | |
| Hydroxyethylcellulose | 0.5 | | | | | |
| Acrylates/C10-30 alkyl acrylate crosspolymer | | | | 0.3 | 0.6 | |
| Cocoatnidopropylbetain | | | 0.3 | | | |
| UVASorb ® K2A | | | | | 2 | |
| Uvinul ® A Plus | 5 | | | | | |
| Butylmethoxydibenzoylmethane | 0.5 | | | 3 | | |
| Disodium phenyldibenzimidazoletetrasulfonate | | 2 | 1 | | | |
| Phenylbenzimidazolesulfonic acid | | 5 | 3 | | 2 | 4 |
| Ethylhexyl methoxycinnamate | 10 | | | | 3 | |
| Diethylhexylbutamidotriazone | | | | 3 | | |
| Ethylhexyltriazone | | | | | 2 | |
| Octocrylene | | | | 5 | | |
| DHAB | 2.5 | 0.75 | 1.5 | 3.0 | 3.5 | 4.0 |
| C₁₂₋₁₅ alkyl benzoate | | | | 3 | | |
| C18-36 triglyceride fatty acid | | | | 1 | | |
| Butylene glycol dicaprylate/dicaprate | 2 | | | | | |
| C12-13 alkyl tartrate | | | | | 5 | |
| Cyclomethicone | 4 | | | 2 | | |
| Insect repellent ® 3535 | | | | 5 | | |
| Dimethicone | | | | 3 | | |
| PVP hexadecene copolymer | | 0.5 | | 1 | | 0.5 |
| Ethylhexyloxyglycerine | | 0.5 | | | | |
| Glycerine | 5 | 7 | 3 | 8 | | S |
| Butylene glycol | | | 5 | | 5 | |
| Metylpropanediol | | | | 4 | | |
| Vitamin E acetate | | 0.3 | 0.2 | 0.5 | | |
| Panthenol | 0.5 | | 0.2 | | | 0.3 |
| Creatinin | | | 0.01 | | 0.02 | |
| Creatin | | | 0.1 | | 0.2 | |
| PEG-40 hydrogenated castor oil | | 0.5 | 0.3 | | | 0.5 |
| Trisodium EDTA | 0.3 | 0.2 | 0.2 | 0.2 | 0.2 | 0.5 |
| Preservatives | q.s. | q.s. | q.s. | q.s. | q.s. | q.s. |
| Sodium hydroxide | q.s. | q.s. | q.s. | q.s. | q.s. | q.s. |
| Perfume, dyes | q.s. | q.s. | q.s. | q.s. | q.s. | q.s. |
| Water | to 100 | to 100 | to 100 | to 100 | to 100 | to 100 |

Example XVI

Cosmetic Foams

|  | A | B | C |
|---|---|---|---|
| Stearic acid | 2 | 2 | |
| Palmitic acid | | | 1.5 |
| Cetyl alcohol | 2.5 | 2 | |
| Stearyl alcohol | | | 3 |
| PEG-100 stearate | | | 3.5 |
| PEG-40 stearate | | 2 | |
| PEG-20 stearate | 3 | | |
| Sorbitan stearate | | 0.8 | |
| C₁₂₋₁₅ alkyl benzoate | 5 | | |
| C₁₂₋₁₃ alkyl tartrate | | | 7 |
| Butylene glycol dicaprylate/dicaprate | | 6 | |
| Dicaprylyl ether | | | 2 |
| Cyclomethicone | | 2 | 3 |
| Butylene glycol | 1 | | |
| Isohexadecane | 2 | | |
| Methylpropanediol | | | |
| Propylene glycol | | | 5 |
| Glycerine | 5 | 7 | |
| UVASorb ® K2A | | | 2 |
| Uvinul ® A Plus | 2 | 3 | |
| DHAB | 0.5 | 1.0 | 1.5 |
| Parsol SLX ® | | | 3 |
| Homosalate | | | 5 |
| Phenylbenzimidazolesulfonic acid | | 2 | 2 |
| Benzophenone-3 | 2 | | |
| Octylsalicylate | | | 5 |
| Octocrylene | 2 | | |
| Bisethylhexyloxyphenol-methoxyphenyltriazine | | 3 | |
| 2,2'-Methylenebis(6-(2H-benzotriazol-2-yl)-4-(1,1,3,3-tetramethylbutyl)phenol) | | | 8 |
| 2,4,6-Tris(biphenyl)-1,3,5-triazine | 5 | | 4 |
| C8-C16 alkylpolyglycoside | 1 | | |
| Vitamin E acetate | 0.6 | 0.5 | 0.2 |
| Creatin/creatinin | | | 0.5 |
| BHT | | | 0.1 |
| Na₂H₂EDTA | | 0.50 | |

-continued

|  | A | B | C |
|---|---|---|---|
| Perfume, preservatives | q.s. | q.s. | q.s. |
| Dyes, etc. | q.s. | q.s. | q.s. |
| Sodium hydroxide | q.s. |  | q.s. |
| Potassium hydroxide |  | q.s. |  |
| Water | to 100.0 | to 100.0 | to 100.0 |

Example XVII

Cosmetic Foams

| Emulsion | D | E | F | G |
|---|---|---|---|---|
| Stearic acid | 2 |  |  |  |
| Palmitic acid |  |  | 3 | 3 |
| Cetyl alcohol | 2 | 2 |  |  |
| Cetylstearyl alcohol |  |  | 2 | 2 |
| Stearyl alcohol |  |  |  |  |
| PEG-100 stearate |  | 4 |  |  |
| PEG-40 stearate | 2 |  |  |  |
| PEG-20 stearate |  |  | 3 | 3 |
| Sorbitan stearate | 0.8 |  |  |  |
| Tridecyl trimellitate |  | 5 |  |  |
| $C_{12-15}$ alkyl benzoate |  |  | 3 | 3 |
| Butylene glycol dicaprylate/dicaprate | 8 |  |  |  |
| Octyldodecanol |  | 2 |  |  |
| Cocoglyceride |  |  |  | 2 |
| Dicaprylyl ether |  |  | 2 | 2 |
| Cyclomethicone |  |  |  |  |
| Dimethicone | 1 |  | 2 | 2 |
| Isohexadecane |  | 3 |  |  |
| Methylpropanediol |  | 4 |  |  |
| Propylene glycol |  |  |  |  |
| Glycerine | 5 |  | 6 | 6 |
| NeoHeliopan ® AP |  | 2 |  |  |
| Phenylbenzimidazole-sulfonic acid | 1 |  |  | 1 |
| DHAB | 0.75 | 1.5 | 3.0 | 6.0 |
| Ethylhexyl methoxycinnamate | 5 |  | 4 | 4 |
| Ethylhexyltriazone |  | 2 |  | 1 |
| Eusolex T-AVO ® | 2 |  |  |  |
| Diethylhexylbutamidotriazone | 1 |  |  |  |
| Butylmethoxydibenzoylmethane | 2.5 |  | 2 | 2 |
| Bisethylhexyloxyphenolmethoxyphenyltriazine | 2 |  |  |  |
| Vitamin E acetate | 0.2 |  | 0.3 | 0.3 |
| $Na_2H_2EDTA$ |  |  |  |  |
| Perfume, preservatives |  |  |  |  |
| Dyes, etc. |  |  |  |  |
| Sodium hydroxide |  | q.s. | q.s. |  |
| Triethanolamine | q.s. |  |  | q.s. |
| Water | to 100.0 | to 100.0 | to 100.0 | to 100.0 |

The invention claimed is:
1. A compound of the formula I

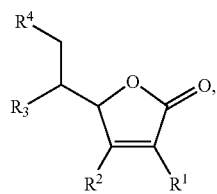

where
R$^1$ or R$^2$ is each, independently of one another, hydroxyl, —O-alkyl, —OC(O)-alkyl, —OPO$_3$M or O-glycosyl,
alkyl is $C_1$—$C_6$-alkyl,
M is an alkali or alkaline-earth metal cation or H,
R$^3$ or R$^4$ are each, independently of one another, hydroxyl or a radical B and
B is a substituent of the formula II, III, IV, V, VII, VIII, IX, and X,

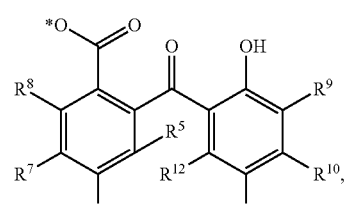

II

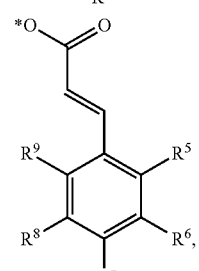

III

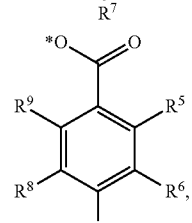

IV

V

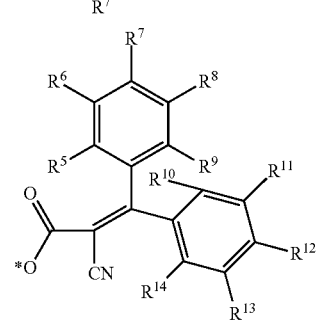

VI

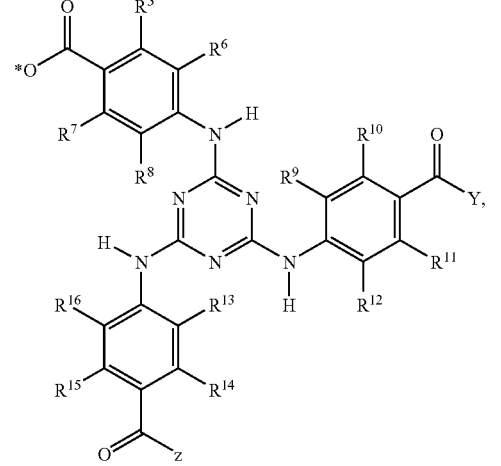

-continued

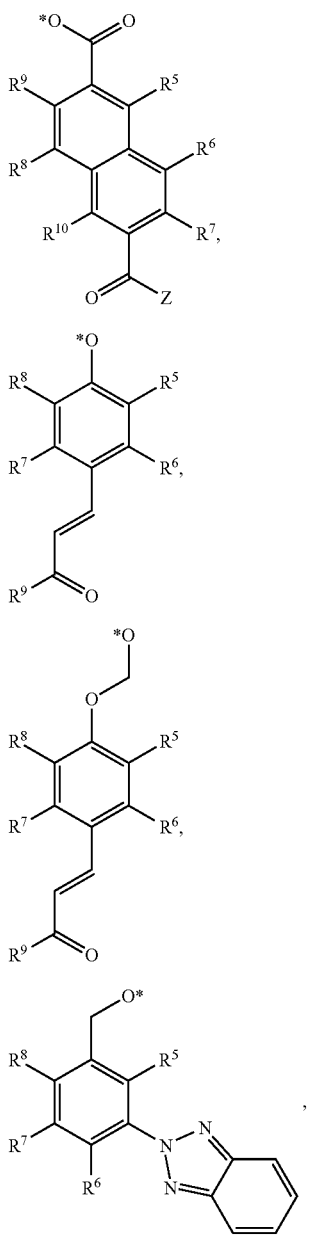

R$^5$ to R$^{14}$ each, independently of one another, denote H, —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl and A is alkyl having 1 to 4 C atoms, n is an integer from 1 to 25, X is the counterion to the cations [NHA$_2$]$^+$ and [NA$_3$]$^+$ or to the anion [SO$_3$]$^-$ and Y and Z are each, independently of one another, -ascorbyl, hydroxyl, —O-2-ethylhexyl, —O-hexyl, —OA or —NH—C(CH$_3$)$_3$, with the proviso that at least one of the radicals R$^3$ or R$^4$ stands for a radical B and with the further provisos that:

when radical B is of formula III, R$^5$, R$^6$, R$^8$ and R$^9$ are H and R$^7$ denotes —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl, and when radical B is of formula IV, R$^5$, R$^6$, R$^8$ and R$^9$ are H and R$^7$ denotes -A, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

2. A compound according to claim 1, wherein R$^2$ in formula I denotes hydroxyl.

3. A compound according to claim 1, wherein R$^1$ in formula I denotes hydroxyl.

4. A compound according to claim 1, wherein radical B is of formula II, R$^5$ to R$^9$, R$^{11}$ and R$^{12}$ denote H and R$^{10}$ is —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —N[NHA$_2$]X, —[NA$_3$]X, —SO$_3$H, —[SO$_3$]X or 2H-benzotriazol-2-yl.

5. A compound according to claim 1, wherein radical B is of formula III, R$^5$, R$^6$, R$^8$ and R$^9$ are H and R$^7$ denotes —OH, —OA, -A, —NH$_2$, —NHA, —NA$_2$, —NH—(CH$_2$—CH$_2$—O)—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

6. A compound according to claim 1, wherein radical B is of formula IV, R$^5$, R$^6$, R$^8$ and R$^9$ are H and R$^7$ denotes -A, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

7. A compound according to claim 1, wherein radical B is of formula V, the substituents R$^6$, R$^8$, R$^{11}$ and R$^{13}$ are H and the substituents R$^5$, R$^7$, R$^9$, R$^{10}$, R$^{12}$ and R$^{14}$ are each, independently of one another, H, —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

8. A compound according to claim 1 wherein radical B is of formula VII, the substituents R$^5$, R$^6$, R$^7$, R$^8$, R$^9$ and R$^{10}$ are H and Z denotes -ascorbyl, hydroxyl, —O-2-ethylhexyl, —O-hexyl, —OA or —NH—C(CH$_3$)$_3$.

9. A compound according to claim 1, wherein radical B is of formula VIII, the substituents R$^5$, R$^6$, R$^7$ and R$^8$ are H and R$^9$ denotes —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

10. A compound according to claim 1, wherein radical B is of formula IX, the substituents R$^5$, R$^6$, R$^7$ and R$^8$ are H and R$^9$ denotes —OH, —OA, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X or 2H-benzotriazol-2-yl.

11. A process for the preparation of a compound according to claim 1, characterised in that a) a compound of the formula XIII

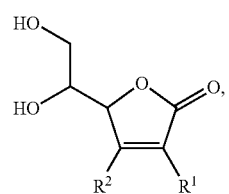

in which

R¹ or R² has a meaning described in claim 18, is reacted directly with a compound of the formula XIV

B-M    XIV in which B has a meaning described in claim 18, and

M denotes an alkali metal or alkaline-earth metal cation or H, or b) the hydroxyl groups of the compound of the formula XIII, as described above, are protected to give a compound of the formula XV

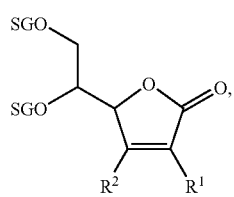

XV in which

R¹ or R² has a meaning described in claim 18, the radicals R¹ and/or R², if these are hydroxyl groups, are subsequently protected by a second protecting group which can be cleaved off again under different reaction conditions to the protecting group SG, the protecting groups SG of the compounds of the formula XV are cleaved off again, and the resultant compound is reacted with a compound of the formula XIV

B-M    XIV, where B has a meaning described in claim 18, and

M denotes an alkali metal or alkaline-earth metal cation or H, and the radicals R¹ and/or R² for the hydroxyl group are subsequently deprotected as hydroxyl group and these hydroxyl groups are, if desired, converted into another radical R¹ or R² ≠OH.

12. An agent comprising at least one compound according to claim 1 and further comprising a cosmetically or pharmacologically compatible vehicle.

13. An agent according to claim 12, characterised in that the at least one compound of the formula I is present in an amount of 0.05 to 10% by weight.

14. An agent according to claim 12, characterised in that at least one further organic UV filter which is able to absorb UV-A and/or UV-B rays is present.

15. An agent according to claim 12, characterised in that at least one inorganic UV filter is present.

16. An agent according claim 12, characterised in that at least one further ascorbic acid derivative, preferably from the group ascorbic acid, magnesium ascorbyl phosphate or ascorbyl palmitate, is present.

17. An agent according to claim 12, characterised in that at least one antioxidant is present.

18. An agent according claim 12, characterised in that at least one antiageing active compound and/or at least one anti-cellulite active compound is present.

19. An agent according to claim 12, characterised in that at least one vitamin derivative is present.

20. An agent according to claim 12, characterised in that at least one further auxiliary, selected from the group thickeners, softeners, moisturisers, surface-active agents, emulsifiers, preservatives, antifoams, perfumes, waxes, lanolin, propellants, dyes and/or pigments which colour the agent itself or the skin, is present.

21. A process for the preparation of an agent according to claim 12, characterised in that said at least one compound of formula I is mixed with a vehicle and optionally with further active compounds or auxiliaries.

22. A compound according to claim 5, wherein $R^7$ is —OA, —$NH_2$, —NHA or —$NA_2$.

23. A compound according to claim 1, wherein radical B is a radical of one of the following formulas:

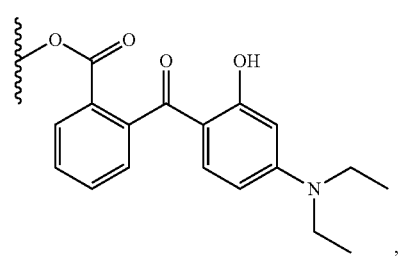

IIa

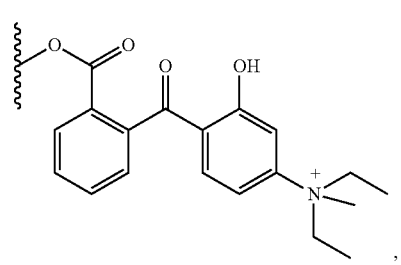

IIb

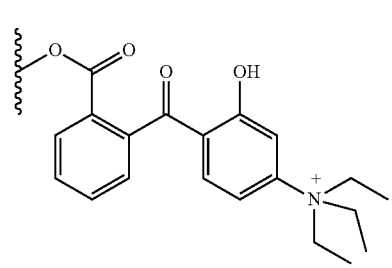

IIc

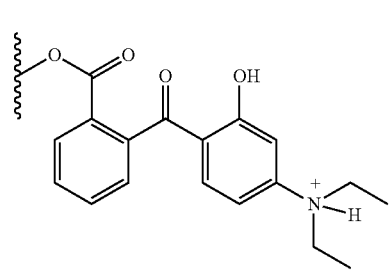

IId

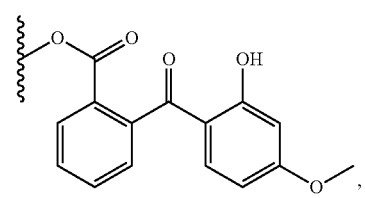

IIe

IIf
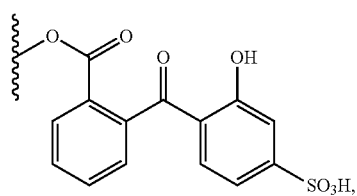
IVa
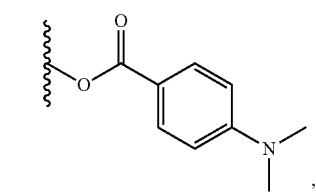
IVc
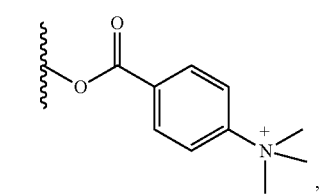
IVd
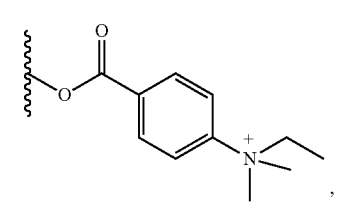
IVe
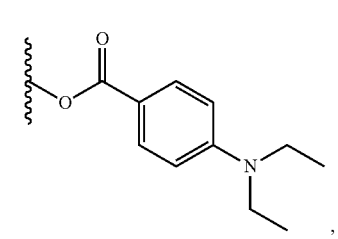
IVf
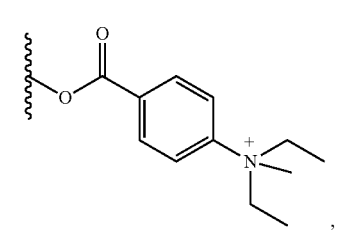
IVg
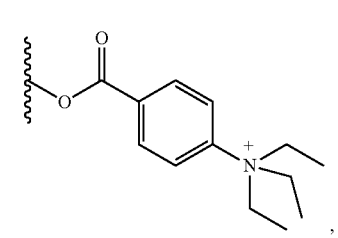
IVh
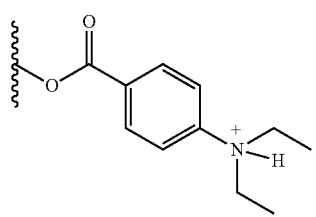
IIIa
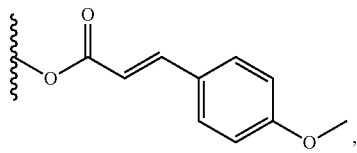
Va
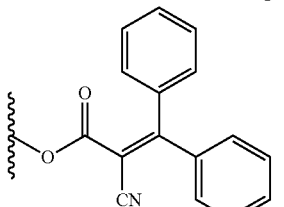
VIIa
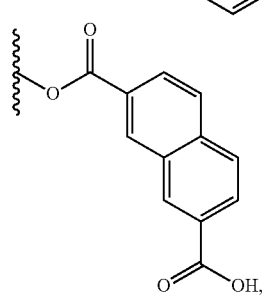
VIIb
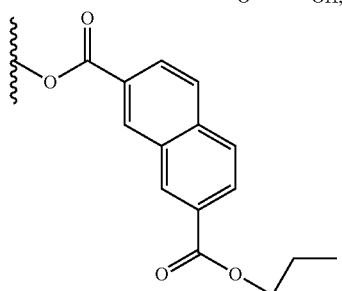
VIIIa
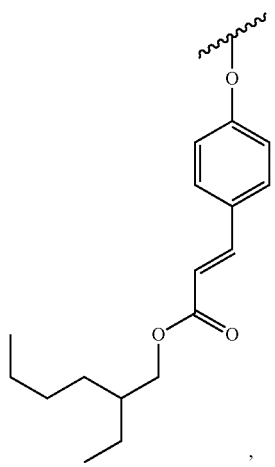

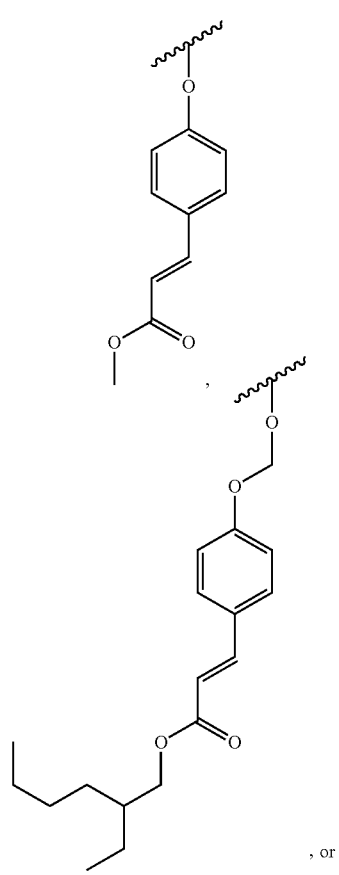
, or
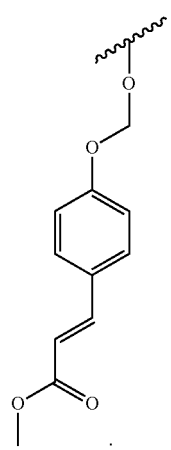
.
24. A process for functionalizing a matrix comprising applying to the matrix at least one ascorbic acid compound of the formula I of claim 1.
25. A process according to claim 24, wherein the matrix is skin, hair or nails.
* * * * *